(12) United States Patent
Sinha et al.

(10) Patent No.: US 12,254,005 B1
(45) Date of Patent: Mar. 18, 2025

(54) SYSTEMS AND METHODS FOR RETRIEVING PATIENT INFORMATION USING LARGE LANGUAGE MODELS

(71) Applicant: nference, Inc., Cambridge, MA (US)

(72) Inventors: Purushottam Sinha, Gaya (IN); Anurag Vij, Bangalore (IN); Jatin Kumar Tomar, Bangalore (IN); Akash Anand, Bhagalpur (IN)

(73) Assignee: nference, Inc., Cambridge, MA (US)

( * ) Notice: Subject to any disclaimer, the term of this patent is extended or adjusted under 35 U.S.C. 154(b) by 0 days.

(21) Appl. No.: 18/622,750

(22) Filed: Mar. 29, 2024

(51) Int. Cl.
| | | |
|---|---|---|
| *G06F 40/40* | (2020.01) | |
| *G06F 16/242* | (2019.01) | |
| *G16H 10/60* | (2018.01) | |
| *G16H 50/70* | (2018.01) | |

(52) U.S. Cl.
CPC .......... *G06F 16/243* (2019.01); *G16H 10/60* (2018.01); *G16H 50/70* (2018.01)

(58) Field of Classification Search
CPC ............ G06F 16/24522; G06F 16/252; G06F 16/3344; G06F 16/345; G06F 40/20; G06F 40/279; G06F 40/284; G06F 40/56; G06F 40/30; G06F 40/40
See application file for complete search history.

(56) References Cited

U.S. PATENT DOCUMENTS

| | | | | |
|---|---|---|---|---|
| 8,812,534 B2* | 8/2014 | Platt | ...................... | G06F 16/242 706/14 |
| 11,960,983 B1* | 4/2024 | Gelfenbeyn | .......... | A63F 13/424 |
| 2003/0088548 A1* | 5/2003 | Kumar | .............. | G06F 16/24534 |
| 2018/0277246 A1* | 9/2018 | Zhong | .................... | A61B 5/746 |
| 2022/0115100 A1* | 4/2022 | Barve | .................... | G16H 10/60 |
| 2022/0293283 A1* | 9/2022 | Subramanian | ......... | G16H 70/00 |
| 2023/0033887 A1 | 2/2023 | Luthra et al. | | |
| 2023/0274086 A1* | 8/2023 | Tunstall-Pedoe | ....... | G06F 40/56 704/9 |
| 2024/0281472 A1* | 8/2024 | LaRhette | .............. | G06F 16/248 |
| 2024/0346256 A1* | 10/2024 | Qin | ........................ | G06F 40/216 |

FOREIGN PATENT DOCUMENTS

| | | |
|---|---|---|
| CN | 116595131 A | 8/2023 |
| CN | 117056493 A | 11/2023 |

\* cited by examiner

*Primary Examiner* — Olujimi A Adesanya
(74) *Attorney, Agent, or Firm* — Caldwell Intellectual Property Law

(57) ABSTRACT

A system for retrieving patient information using large language models including a computing device configured to receive a natural language query as a function of a user input, input the natural language query into a large language model communicatively connected to the least a processor, receive a computer language query comprising a plurality of nodes from the large language model, map the plurality of nodes to one or more entries in a patient database, receive a database response from the patient database as a function of the mapping, generate a final database query as a function of the database response. query the patient database using the final database query, receive a user response as a function of the final database query, and transmit the user response to a graphical user interface as a function of the final database query.

14 Claims, 8 Drawing Sheets

SYSTEMS AND METHODS FOR RETRIEVING PATIENT INFORMATION USING LARGE LANGUAGE MODELS

FIELD OF THE INVENTION

The present invention generally relates to the field of data management and machine learning. In particular, the present invention is directed to systems and methods for retrieving patient information using large language models.

BACKGROUND

The retrieval of patient information from databases requires queries to be made in computer language formats. In addition, retrieved data may not be fully encompassing, and as a result, some entries may be overlooked or not found. Current systems that do not require computer language formats to be used for queries are lacking and do not provide for adequate data retrieval.

SUMMARY OF THE DISCLOSURE

In an aspect a system for retrieving patient information using large language models is described. The system includes at least a processor and a memory communicatively connected to the at least a processor. The memory contains instructions configuring the at least a processor to receive a natural language query as a function of a user input, input the natural language query into a large language model communicatively connected to the least a processor, receive a computer language query including a plurality of nodes from the large language model, map the plurality of nodes to one or more entries in a patient database, receive a database response from the patient database as a function of the mapping, generate a final database query as a function of the database response, query the patient database using the final database query, receive a user response as a function of the final database query and transmit the user response to a graphical user interface as a function of the final database query.

In another aspect a method for retrieving patient information using large language models is described, the method includes receiving, by at least a processor, a natural language query as a function of a user input, inputting, by the at least a processor, the natural language query into a large language model communicatively connected to the least a processor, receiving, by the at least a processor, a computer language query including a plurality of nodes from the large language model, mapping, by the at least a processor, the plurality of nodes to one or more entries in a patient database, receiving, by the at least a processor, a database response from the patient database as a function of the mapping, generating, by the at least a processor, a final database query as a function of the database response, querying, by the at least a processor, the patient database using the final database query, receiving by the at least a processor, a user response as a function of the final database query and transmitting, by the at least a processor, the user response to a graphical user interface as a function of the final database query.

These and other aspects and features of non-limiting embodiments of the present invention will become apparent to those skilled in the art upon review of the following description of specific non-limiting embodiments of the invention in conjunction with the accompanying drawings.

BRIEF DESCRIPTION OF THE DRAWINGS

For the purpose of illustrating the invention, the drawings show aspects of one or more embodiments of the invention. However, it should be understood that the present invention is not limited to the precise arrangements and instrumentalities shown in the drawings, wherein.

The drawings are not necessarily to scale and may be illustrated by phantom lines, diagrammatic representations and fragmentary views. In certain instances, details that are not necessary for an understanding of the embodiments or that render other details difficult to perceive may have been omitted.

DETAILED DESCRIPTION

At a high level, aspects of the present disclosure are directed to systems and methods for retrieving patient information using large language models in accordance with the subject disclosure. In one or more embodiments, systems and methods described herein may be used to retrieve patient information from a remote database using large language models. In an aspect, large language models may be utilized to generate queries in order to query a database for entries within a database wherein large language models may be used to retrieve entries following queries.

Figure 1:
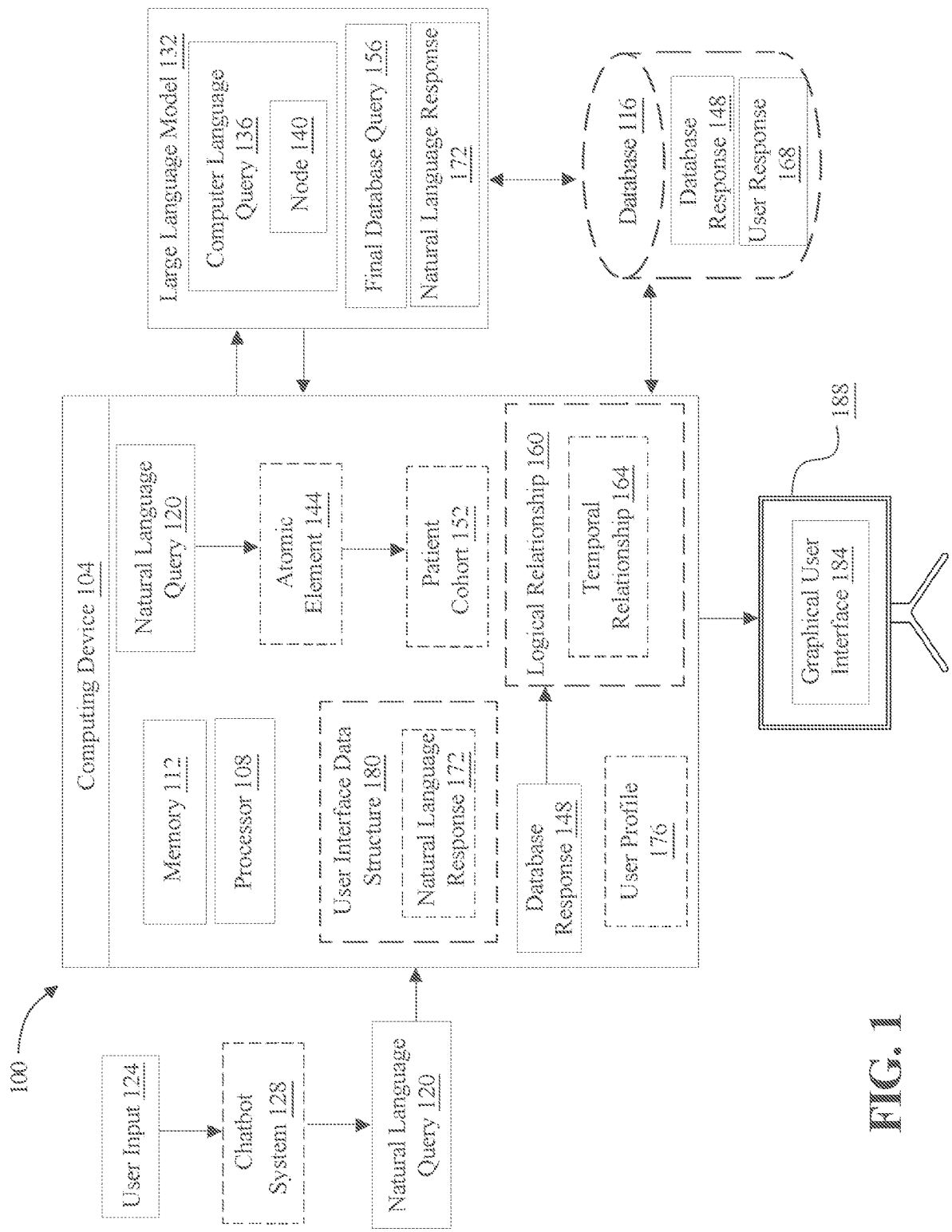
FIG. 1 is an exemplary embodiment of a system for retrieving patient information using large language models in accordance with the subject disclosure.

Referring now to FIG. 1, A system for retrieving patient information using large language models is described. System 100 includes a computing device 104. System 100 includes a processor 108. Processor 108 may include, without limitation, any processor 108 described in this disclosure. Processor 108 may be included in a and/or consistent with computing device 104. In one or more embodiments, processor 108 may include a multi-core processor. In one or more embodiments, multi-core processor may include multiple processor cores and/or individual processing units. "Processing unit" for the purposes of this disclosure is a device that is capable of executing instructions and performing calculations for a computing device 104. In one or more embodiments, processing units may retrieve instructions from a memory, decode the data, secure functions and transmit the functions back to the memory. In one or more embodiments, processing units may include an arithmetic logic unit (ALU) wherein the ALU is responsible for carrying out arithmetic and logical operations. This may include, addition, subtraction, multiplication, comparing two data, contrasting two data and the like. In one or more embodiments, processing unit may include a control unit wherein the control unit manages execution of instructions such that they are performed in the correct order. In none or more embodiments, processing unit may include registers wherein the registers may be used for temporary storage of data such as inputs fed into the processor and/or outputs executed by the processor. In one or more embodiments, processing unit may include cache memory wherein memory may be retrieved from cache memory for retrieval of data. In one or more embodiments, processing unit may include a clock register wherein the clock register is configured to synchronize the processor with other computing components. In one or more embodiments, processor 108 may include more than one processing unit having at least one or more arithmetic and logic units (ALUs) with hardware components that may perform arithmetic and logic operations. Processing units may further include registers to hold operands and results, as well as potentially "reservation station" queues of registers, registers to store interim results in multi-cycle operations, and an instruction unit/control circuit (including e.g. a finite state machine and/or multiplexor) that reads op codes from program instruction register banks and/or receives those op codes and enables registers/arithmetic and logic operators to read/output values. In one or more embodiments, processing unit may include a floating-point unit (FPU) wherein the FPU is configured to handle arithmetic operations with floating point numbers. In one or more embodiments, processor 108 may include a plurality of processing units wherein each processing unit may be configured for a particular task and/or function. In one or more embodiments, each core within multi-core processor may function independently. In one or more embodiments, each core within multi-core processor may perform functions in parallel with other cores. In one or more embodiments, multi-core processor may allow for a dedicated core for each program and/or software running on a computing system. In one or more embodiments, multiple cores may be used for a singular function and/or multiple functions. In one or more embodiments, multi-core processor may allow for a computing system to perform differing functions in parallel. In one or more embodiments, processor 108 may include a plurality of multi-core processors. Computing device 104 may include any computing device as described in this disclosure, including without limitation a microcontroller, microprocessor, digital signal processor (DSP) and/or system on a chip (SoC) as described in this disclosure. Computing device 104 may include, be included in, and/or communicate with a mobile device such as a mobile telephone or smartphone. Computing device 104 may include a single computing device 104 operating independently or may include two or more computing devices operating in concert, in parallel, sequentially or the like; two or more computing devices may be included together in a single computing device 104 or in two or more computing devices. Computing device 104 may interface or communicate with one or more additional devices as described below in further detail via a network interface device. Network interface device may be utilized for connecting computing device 104 to one or more of a variety of networks, and one or more devices. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network may employ a wired and/or a wireless mode of communication. In general, any network topology may be used. Information (e.g., data, software etc.) may be communicated to and/or from a computer and/or a computing device 104. Computing device 104 may include but is not limited to, for example, a computing device 104 or cluster of computing devices in a first location and a second computing device 104 or cluster of computing devices in a second location. Computing device 104 may include one or more computing devices dedicated to data storage, security, distribution of traffic for load balancing, and the like. Computing device 104 may distribute one or more computing tasks as described below across a plurality of computing devices of computing device 104, which may operate in parallel, in series, redundantly, or in any other manner used for distribution of tasks or memory 112 between computing devices. Computing device 104 may be implemented, as a non-limiting example, using a "shared nothing" architecture.

With continued reference to FIG. 1, computing device 104 may be designed and/or configured to perform any method, method step, or sequence of method steps in any embodiment described in this disclosure, in any order and with any degree of repetition. For instance, computing device 104 may be configured to perform a single step or sequence repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. Computing device 104 may perform any step or sequence of steps as described in this disclosure in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

With continued reference to FIG. 1, computing device 104 may perform determinations, classification, and/or analysis steps, methods, processes, or the like as described in this disclosure using machine-learning processes. A "machine-learning process," as used in this disclosure, is a process that automatedly uses a body of data known as "training data" and/or a "training set" (described further below in this disclosure) to generate an algorithm that will be performed by a Processor module to produce outputs given data provided as inputs; this is in contrast to a non-machine learning software program where the commands to be executed are determined in advance by a user and written in a programming language. A machine-learning process may utilize supervised, unsupervised, lazy-learning processes and/or neural networks, described further below.

With continued reference to FIG. 1, system 100 includes a memory 112 communicatively connected to processor 108, wherein the memory 112 contains instructions configuring processor 108 to perform any processing steps as described herein. As used in this disclosure, "communicatively connected" means connected by way of a connection, attachment, or linkage between two or more relata which allows for reception and/or transmittance of information therebetween. For example, and without limitation, this connection may be wired or wireless, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. A communicative connection may be achieved, for example and without limitation, through wired or wireless electronic, digital, or analog, communication, either directly or by way of one or more intervening devices or components. Further, communicative connection may include electrically coupling or connecting at least an output of one device, component, or circuit to at least an input of another device, component, or circuit. For example, and without limitation, using a bus or other facility for intercommunication between elements of a computing device 104. Communicative connecting may also include indirect connections via, for example and without limitation, wireless connection, radio communication, low power wide area network, optical communication, magnetic, capacitive, or optical coupling, and the like. In some instances, the terminology "communicatively coupled" may be used in place of communicatively connected in this disclosure.

With continued reference to FIG. 1, memory 112 may include a primary memory and a secondary memory. "Primary memory" also known as "random access memory" (RAM) for the purposes of this disclosure is a short-term storage device in which information is processed. In one or more embodiments, during use of computing device 104, instructions and/or information may be transmitted to primary memory wherein information may be processed. In one or more embodiments, information may only be populated within primary memory while a particular software is running. In one or more embodiments, information within primary memory is wiped and/or removed after computing device 104 has been turned off and/or use of a software has been terminated. In one or more embodiments, primary memory may be referred to as "Volatile memory" wherein the volatile memory only holds information while data is being used and/or processed. In one or more embodiments, volatile memory may lose information after a loss of power. "Secondary memory" also known as "storage," "hard disk drive" and the like for the purposes of this disclosure is a long-term storage device in which an operating system and other information is stored. In one or remote embodiments, information may be retrieved from secondary memory and transmitted to primary memory during use. In one or more embodiments, secondary memory may be referred to as non-volatile memory wherein information is preserved even during a loss of power. In one or more embodiments, data within secondary memory cannot be accessed by processor. In one or more embodiments, data is transferred from secondary to primary memory wherein processor 108 may access the information from primary memory.

Still referring to FIG. 1, System 100 may include a database 116. Database may include a remote database 116. Database 116 may be implemented, without limitation, as a relational database, a key-value retrieval database such as a NOSQL database, or any other format or structure for use as database that a person skilled in the art would recognize as suitable upon review of the entirety of this disclosure. Database may alternatively or additionally be implemented using a distributed data storage protocol and/or data structure, such as a distributed hash table or the like. Database 116 may include a plurality of data entries and/or records as described above. Data entries in database may be flagged with or linked to one or more additional elements of information, which may be reflected in data entry cells and/or in linked tables such as tables related by one or more indices in a relational database. Persons skilled in the art, upon reviewing the entirety of this disclosure, will be aware of various ways in which data entries in database may store, retrieve, organize, and/or reflect data and/or records.

With continued reference to FIG. 1, system 100 may include and/or be communicatively connected to a server, such as but not limited to, a remote server, a cloud server, a network server and the like. In one or more embodiments. In one or more embodiments, computing device 104 may be configured to transmit one or more processes to be executed by server. In one or more embodiments, server may contain additional and/or increased processor power wherein one or more processes as described below may be performed by server. For example, and without limitation, one or more processes associated with machine learning may be performed by network server, wherein data is transmitted to server, processed and transmitted back to computing device. In one or more embodiments, server may be configured to perform one or more processes as described below to allow for increased computational power and/or decreased power usage by system computing device 104. In one or more embodiments, computing device 104 may transmit processes to server wherein computing device 104 may conserve power or energy.

With continued reference to FIG. 1, processor 108 is configured to receive a natural language query 120 as a function of a user input 124. A "language query" for the purposes of this disclosure is a request made to receive information using human language. For example, and without limitation, natural language query 120 made include a request such as "Grab information pertaining to X." wherein the request may be made in the form of ordinary human language. In contrast, a data language query may include a request in a data language format such as SQL or code. In one or more embodiments, natural language query 120 may include a request made through ordinary human interaction with a computing device 104. A "natural language query" for the purposes of this disclosure is a natural language query 120 for medical information about one or more individuals. For example, and without limitation, natural language query 120 may include a request to receive information about a medical patient, request to receive individuals within a particular health disorder and the like. In one or more embodiments natural language query 120 may include a request to receive medical information associated with one or more individuals, such as but not limited to, names, ages, genders, medical history, medications taken, diagnosis, treatment given, treatment refused, future treatment that will be provided and the like. In one or more embodiments, natural language query 120 may include a request to receive any information that may be contained within an electronic health record. As used in this disclosure, an "electronic health record (EHR)" is a digital collection of health information about individual patients and/or populations. In an embodiment, electronic health records may include medical histories, treatment plans, progress notes, laboratory results, and the like.

With continued reference to FIG. 1, natural language query 120 may include a request made by an individual using ordinary everyday human language as opposed to request within a data format. For example, and without limitation, natural language query 120 may include a request in the form of a sentence, a question, a sentence in the form of a conversation and the like. In one or more embodiments, natural language query 120 may include a request made similar to that made from one individual to another in a physical world setting. In one or more embodiments, natural language query 120 may include requests such as but not limited to, "what were the results of the patients last MRI." In one or more embodiments, natural language query 120 may be generated by a user. A "user" for the purposes of this disclosure is an individual interacting with system 100. For example, and without limitation, user may include a medical professional seeking medical information about an individual, a medical technician, a nurse, an individual seeking information about themselves and the like.

In one or more embodiments, natural language query 120 may be received as a function of user input 124. A "user input" for the purposes of this disclosure is information received by computing device 104 from a user. In one or more embodiments, user input 124 may include the selection of characters on a keyboard, the movement of a mouse, interactions with a display device, communications made through a microphone, a camera and the like. In one or more embodiments, user input 124 may be made through a remote device separate from computing device 104, such as but not limited to, a desktop, a laptop computer, a smartphone, a smart watch and/or any computing system capable of interacting with system 100.

In one or more embodiments, natural language query 120 may be received through a chatbot system 128. A "chatbot system" for the purposes of this disclosure is a program configured to simulate human interaction with a user in order to receive or convey information. In some cases, chatbot system 128 may be configured to receive natural language query 120 and/or elements thereof and any other data as described in this disclosure through interactive questions presented to the user. In one or more embodiments, chatbot system 128 may be configured to simulate human interaction wherein chatbot system 128 may present questions in responses in a natural language format. In one or more embodiments, chatbot system 128 may be configured to simulate human interaction in a variety of languages based on the preferences of a user. In one or more embodiments, while data processing and/or information received may be in a particular language, chatbot may be configured to translate data based on the preferences of the user. In one or more embodiments, interactions within chatbot system 128 may be received as a natural language query 120. This may be described in further detail below.

With continued reference to FIG. 1, user input 124 may further include electronic health records and/or any other medical information associated with a patient. In one or more embodiments, information may be received from one or more users and stored on database wherein natural language medical database query may include a request to receive information from database. In one or more embodiments, processor 108 may be configured to receive unstructured data to be placed within database wherein data may be received as a function of a natural language query 120. In one or more embodiments, unstructured data may be used to generate responses to natural language medical database query. In one or more embodiments, database may include a patient database wherein patient database may include electronic health records and/or any other medical information associated with an individual and/or medical patient. As used in the current disclosure, "unstructured data" is any type of information that doesn't have a pre-defined data model or is not organized in a predefined manner. In an exemplary embodiment, unstructured data may be textual data, multimedia content (e.g., audio files, images, and/or videos), electronic messages, and the like. Textual data may include emails, documents, articles, and any other text-based content. In an exemplary embodiment, unstructured data may be unstructured clinical data. As used in this disclosure, "clinical data" is information related to the health and medical history of individuals collected during the course of patient care. This data may be useful for healthcare professionals, researchers, and institutions to make informed decisions about diagnosis, treatment, and patient outcomes. In an exemplary embodiment, unstructured clinical data may include physician's notes, patient histories, diagnostic reports, and other textural data that are not formatted or categorized. As used in this disclosure, an "electronic record" is information that is stored and managed in a digital format. These records can encompass a wide range of content, including text documents, spreadsheets, databases 116, emails, images, audio files, and more. In an embodiment, electronic record may be an electronic health record.

Continuing to refer to FIG. 1, in one or more embodiments, processor 108 may be configured to receive unstructured data and/or electronic records from user input 124. In one or more embodiments, user input 124 may include interaction of user input 124 device such as uploading an electronic record and the like. In an embodiment, user input 124 device may be any computing device 104 described herein that is communicatively connected to system 100.

With continued reference to FIG. 1, processor 108 may be configured to receive unstructured data and/or electronic records using an application programming interface (API). As used herein, an "application programming interface" is a set of functions that allow applications to access data and interact with external software components, operating systems, or microdevices, such as another web application or computing device 104. An API may define the methods and data formats that applications can use to request and exchange information. APIs enable seamless integration and functionality between different systems, applications, or platforms. An API may deliver unstructured data and/or electronic records to system 100 from a system/application that is associated with a user, medical provider, or other third party custodian of user information. An API may be configured to query web applications or other websites to retrieve unstructured data and/or electronic records.

With continued reference to FIG. 1, processor 108 may retrieve unstructured data and/or electronic records from one or more sources using a web crawler. A "web crawler," as used herein, is a program that systematically browses the internet for the purpose of Web indexing. The web crawler may be seeded with platform URLs, wherein the crawler may then visit the next related URL, retrieve the content, index the content, and/or measures the relevance of the content to the topic of interest. In some embodiments, processor 108 may generate a web crawler to scrape data associated with the user from user related social media and networking platforms. The web crawler may be seeded and/or trained with a user's social media handles, name, and common platforms a user is active on. The web crawler may be trained with information received from a user through a user interface, described below. Processor 108 may receive information such as a user's name, platform handles, platforms associated with the user and the like, from the user interface. In some embodiments, user database may be populated with data associated with the first user and the second user received from the user interface. A web crawler may be generated by a processor 108. In some embodiments, a web crawler may be configured to generate a web query. A web query may include search criteria. Search criteria may include photos, videos, audio, user account handles, web page addresses and the like received from the user. A web crawler function may be configured to search for and/or detect one or more data patterns. A "data pattern" as used in this disclosure is a matched characteristic of a plurality of information. For example, a data pattern may include, but is not limited to, features, phrases, repeated words, repeated data elements, overlapping classes of data elements, and the like as described further below in this disclosure. The web crawler may work in tandem with any machine-learning model, digital processing technique utilized by processor 108, and the like as described in this disclosure. In some embodiments, a web crawler may be configured to determine the relevancy of a data pattern. Relevancy may be determined by a relevancy score. A relevancy score may be automatically generated by a processor 108, received from a machine learning model, and/or received from the user. In some embodiments, a relevancy score may include a range of numerical values that may correspond to a relevancy strength of data received from a web crawler function. As a non-limiting example, a web crawler function may search the Internet for photographs of the user based on one or more photographs received from an entity. The web crawler may return data results of photos of patients and the like.

Continuing to refer to FIG. 1, processor 108 may extract unstructured data from electronic records or other text received from the user using an optical character recognition system. Optical character recognition or optical character reader (OCR) may be applied upon submission of electronic records into processor 108 and includes automatic conversion of images of written information (e.g., typed, handwritten or printed text) into machine-encoded text. In some cases, recognition of at least a keyword from an image component may include one or more processes, including without limitation OCR, optical word recognition, intelligent character recognition, intelligent word recognition, and the like. In some cases, OCR may recognize written text, one glyph or character at a time. In some cases, optical word recognition may recognize written text, one word at a time, for example, for languages that use a space as a word divider. In some cases, intelligent character recognition (ICR) may recognize written text one glyph or character at a time, for instance by employing machine learning processes. In some cases, intelligent word recognition (IWR) may recognize written text, one word at a time, for instance by employing machine learning processes.

Still referring to FIG. 1, in some cases OCR may be an "offline" process, which analyses a static document or image frame. In some cases, handwriting movement analysis can be used as input to handwriting recognition. For example, instead of merely using shapes of glyphs and words, this technique may capture motions, such as the order in which segments are drawn, the direction, and the pattern of putting the pen down and lifting it. This additional information can make handwriting recognition more accurate. In some cases, this technology may be referred to as "online" character recognition, dynamic character recognition, real-time character recognition, and intelligent character recognition.

Still referring to FIG. 1, in some cases, OCR processes may employ pre-processing of image component. Pre-processing process may include without limitation de-skew, de-speckle, binarization, line removal, layout analysis or "zoning," line and word detection, script recognition, character isolation or "segmentation," and normalization. In some cases, a de-skew process may include applying a transform (e.g., homography or affine transform) to image component to align text. In some cases, a de-speckle process may include removing positive and negative spots and/or smoothing edges. In some cases, a binarization process may include converting an image from color or greyscale to black-and-white (i.e., a binary image). Binarization may be performed as a simple way of separating text (or any other desired image component) from a background of image component. In some cases, binarization may be required for example if an employed OCR algorithm only works on binary images. In some cases, a line removal process may include removal of non-glyph or non-character imagery (e.g., boxes and lines). In some cases, a layout analysis or "zoning" process may identify columns, paragraphs, captions, and the like as distinct blocks. In some cases, a line and word detection process may establish a baseline for word and character shapes and separate words, if necessary. In some cases, a script recognition process may, for example in multilingual documents, identify script allowing an appropriate OCR algorithm to be selected. In some cases, a character isolation or "segmentation" process may separate signal characters, for example character-based OCR algorithms. In some cases, a normalization process may normalize aspect ratio and/or scale of image component.

Still referring to FIG. 1, in some embodiments an OCR process will include an OCR algorithm. Exemplary OCR algorithms include matrix matching process and/or feature extraction processes. Matrix matching may involve comparing an image to a stored glyph on a pixel-by-pixel basis. In some case, matrix matching may also be known as "pattern matching," "pattern recognition," and/or "image correlation." Matrix matching may rely on an input glyph being correctly isolated from the rest of the image component. Matrix matching may also rely on a stored glyph being in a similar font and at a same scale as input glyph. Matrix matching may work best with typewritten text.

Still referring to FIG. 1, in some embodiments, an OCR process may include a feature extraction process. In some cases, feature extraction may decompose a glyph into features. Exemplary non-limiting features may include corners, edges, lines, closed loops, line direction, line intersections, and the like. In some cases, feature extraction may reduce dimensionality of representation and may make the recognition process computationally more efficient. In some cases, extracted feature can be compared with an abstract vector-like representation of a character, which might reduce to one or more glyph prototypes. General techniques of feature detection in computer vision are applicable to this type of OCR. In some embodiments, machine-learning processes like nearest neighbor classifiers (e.g., k-nearest neighbors algorithm) can be used to compare image features with stored glyph features and choose a nearest match. OCR may employ any machine-learning process described in this disclosure, for example machine-learning processes described with reference to FIG. 2. Exemplary non-limiting OCR software includes Cuneiform and Tesseract. Cuneiform is a multi-language, open-source optical character recognition system originally developed by Cognitive Technologies of Moscow, Russia. Tesseract is free OCR software originally developed by Hewlett-Packard of Palo Alto, California, United States.

Still referring to FIG. 1, in some cases, OCR may employ a two-pass approach to character recognition. Second pass may include adaptive recognition and use letter shapes recognized with high confidence on a first pass to recognize better remaining letters on the second pass. In some cases, two-pass approach may be advantageous for unusual fonts or low-quality image components where visual verbal content may be distorted. Another exemplary OCR software tool includes OCRopus. OCRopus development is led by German Research Centre for Artificial Intelligence in Kaiserslautern, Germany.

Still referring to FIG. 1, in some cases, OCR may include post-processing. For example, OCR accuracy can be increased, in some cases, if output is constrained by a lexicon. A lexicon may include a list or set of words that are allowed to occur in a document. In some cases, a lexicon may include, for instance, all the words in the English language, or a more technical lexicon for a specific field. In some cases, an output stream may be a plain text stream or file of characters. In some cases, an OCR process may preserve an original layout of visual verbal content. In some cases, near-neighbor analysis can make use of co-occurrence frequencies to correct errors, by noting that certain words are often seen together. For example, "Washington, D.C." is generally far more common in English than "Washington DOC." In some cases, an OCR process may make us of a priori knowledge of grammar for a language being recognized. For example, grammar rules may be used to help determine if a word is likely to be a verb or a noun. Distance conceptualization may be employed for recognition and classification. For example, a Levenshtein distance algorithm may be used in OCR post-processing to further optimize results.

With continued reference to FIG. 1, processor 108 is configured to transmit and/or input natural language query 120 into a large language model communicatively connected to processor 108. A "large language model," as used herein, is a deep learning data structure that can recognize, summarize, translate, predict and/or generate text and other content based on knowledge gained from massive datasets. Large language models may be trained on large sets of data. Training sets may be drawn from diverse sets of data such as, as non-limiting examples, novels, blog posts, articles, emails, unstructured data, electronic records, and the like. In some embodiments, training sets may include a variety of subject matters, such as, as nonlimiting examples, medical report documents, electronic health records, entity documents, business documents, inventory documentation, emails, user communications, advertising documents, newspaper articles, and the like. In some embodiments, training sets of an LLM 132 may include information from one or more public or private databases 116. As a non-limiting example, training sets may include databases 116 associated with an entity. In some embodiments, training sets may include portions of documents associated with the electronic records correlated to examples of outputs. In an embodiment, an LLM 132 may include one or more architectures based on capability requirements of an LLM 132. Exemplary architectures may include, without limitation, GPT (Generative Pretrained Transformer), BERT (Bidirectional Encoder Representations from Transformers), T5 (Text-To-Text Transfer Transformer), and the like. Architecture choice may depend on a needed capability such generative, contextual, or other specific capabilities.

With continued reference to FIG. 1, in some embodiments, an LLM 132 may be generally trained. As used in this disclosure, a "generally trained" LLM 132 is an LLM 132 that is trained on a general training set comprising a variety of subject matters, data sets, and fields. In some embodiments, an LLM 132 may be initially generally trained. Additionally, or alternatively, an LLM 132 may be specifically trained. As used in this disclosure, a "specifically trained" LLM 132 is an LLM 132 that is trained on a specific training set, wherein the specific training set includes data including specific correlations for the LLM 132 to learn. As a non-limiting example, an LLM 132 may be generally trained on a general training set, then specifically trained on a specific training set. In an embodiment, specific training of an LLM 132 may be performed using a supervised machine learning process. In some embodiments, generally training an LLM 132 may be performed using an unsupervised machine learning process. As a non-limiting example, specific training set may include information from a database 116. As a non-limiting example, specific training set may include text related to the users such as user specific data for electronic records correlated to examples of outputs. In an embodiment, training one or more machine learning models may include setting the parameters of the one or more models (weights and biases) either randomly or using a pretrained model. Generally training one or more machine learning models on a large corpus of text data can provide a starting point for fine-tuning on a specific task. A model such as an LLM 132 may learn by adjusting its parameters during the training process to minimize a defined loss function, which measures the difference between predicted outputs and ground truth. Once a model has been generally trained, the model may then be specifically trained to fine-tune the pretrained model on task-specific data to adapt it to the target task. Fine-tuning may involve training a model with task-specific training data, adjusting the model's weights to optimize performance for the particular task. In some cases, this may include optimizing the model's performance by fine-tuning hyperparameters such as learning rate, batch size, and regularization. Hyperparameter tuning may help in achieving the best performance and convergence during training. In an embodiment, fine-tuning a pretrained model such as an LLM 132 may include fine-tuning the pretrained model using Low-Rank Adaptation (LoRA). As used in this disclosure, "Low-Rank Adaptation" is a training technique for large language models that modifies a subset of parameters in the model. Low-Rank Adaptation may be configured to make the training process more computationally efficient by avoiding a need to train an entire model from scratch. In an exemplary embodiment, a subset of parameters that are updated may include parameters that are associated with a specific task or domain.

With continued reference to FIG. 1, in some embodiments an LLM 132 may include and/or be produced using Generative Pretrained Transformer (GPT), GPT-2, GPT-3, GPT-4, and the like. GPT, GPT-2, GPT-3, GPT-3.5, and GPT-4 are products of Open AI Inc., of San Francisco, CA. An LLM 132 may include a text prediction based algorithm configured to receive an article and apply a probability distribution to the words already typed in a sentence to work out the most likely word to come next in augmented articles. For example, if some words that have already been typed are "Nice to meet", then it may be highly likely that the word "you" will come next. An LLM 132 may output such predictions by ranking words by likelihood or a prompt parameter. For the example given above, an LLM 132 may score "you" as the most likely, "your" as the next most likely, "his" or "her" next, and the like. An LLM 132 may include an encoder component and a decoder component.

Still referring to FIG. 1, an LLM 132 may include a transformer architecture. In some embodiments, encoder component of an LLM 132 may include transformer architecture. A "transformer architecture," for the purposes of this disclosure is a neural network architecture that uses self-attention and positional encoding. Transformer architecture may be designed to process sequential input data, such as natural language, with applications towards tasks such as translation and text summarization. Transformer architecture may process the entire input all at once. "Positional encoding," for the purposes of this disclosure, refers to a data processing technique that encodes the location or position of an entity in a sequence. In some embodiments, each position in the sequence may be assigned a unique representation. In some embodiments, positional encoding may include mapping each position in the sequence to a position vector. In some embodiments, trigonometric functions, such as sine and cosine, may be used to determine the values in the position vector. In some embodiments, position vectors for a plurality of positions in a sequence may be assembled into a position matrix, wherein each row of position matrix may represent a position in the sequence.

With continued reference to FIG. 1, an LLM 132 and/or transformer architecture may include an attention mechanism. An "attention mechanism," as used herein, is a part of a neural architecture that enables a system to dynamically quantify the relevant features of the input data. In the case of natural language processing, input data may be a sequence of textual elements. It may be applied directly to the raw input or to its higher-level representation.

With continued reference to FIG. 1, attention mechanism may represent an improvement over a limitation of an encoder-decoder model. An encoder-decider model encodes an input sequence to one fixed length vector from which the output is decoded at each time step. This issue may be seen as a problem when decoding long sequences because it may make it difficult for the neural network to cope with long sentences, such as those that are longer than the sentences in the training corpus. Applying an attention mechanism, an LLM 132 may predict the next word by searching for a set of positions in a source sentence where the most relevant information is concentrated. An LLM 132 may then predict the next word based on context vectors associated with these source positions and all the previously generated target words, such as textual data of a dictionary correlated to a prompt in a training data set. A "context vector," as used herein, are fixed-length vector representations useful for document retrieval and word sense disambiguation.

Still referring to FIG. 1, attention mechanism may include, without limitation, generalized attention self-attention, multi-head attention, additive attention, global attention, and the like. In generalized attention, when a sequence of words or an image is fed to an LLM 132, it may verify each element of the input sequence and compare it against the output sequence. Each iteration may involve the mechanism's encoder capturing the input sequence and comparing it with each element of the decoder's sequence. From the comparison scores, the mechanism may then select the words or parts of the image that it needs to pay attention to. In self-attention, an LLM 132 may pick up particular parts at different positions in the input sequence and over time compute an initial composition of the output sequence. In multi-head attention, an LLM 132 may include a transformer model of an attention mechanism. Attention mechanisms, as described above, may provide context for any position in the input sequence. For example, if the input data is a natural language sentence, the transformer does not have to process one word at a time. In multi-head attention, computations by an LLM 132 may be repeated over several iterations, each computation may form parallel layers known as attention heads. Each separate head may independently pass the input sequence and corresponding output sequence element through a separate head. A final attention score may be produced by combining attention scores at each head so that every nuance of the input sequence is taken into consideration. In additive attention (Bahdanau attention mechanism), an LLM 132 may make use of attention alignment scores based on a number of factors. Alignment scores may be calculated at different points in a neural network, and/or at different stages represented by discrete neural networks. Source or input sequence words are correlated with target or output sequence words but not to an exact degree. This correlation may take into account all hidden states and the final alignment score is the summation of the matrix of alignment scores. In global attention (Luong mechanism), in situations where neural machine translations are required, an LLM 132 may either attend to all source words or predict the target sentence, thereby attending to a smaller subset of words.

With continued reference to FIG. 1, multi-headed attention in encoder may apply a specific attention mechanism called self-attention. Self-attention allows models such as an LLM 132 or components thereof to associate each word in the input, to other words. As a non-limiting example, an LLM 132 may learn to associate the word "you", with "how" and "are". It's also possible that an LLM 132 learns that words structured in this pattern are typically a question and to respond appropriately. In some embodiments, to achieve self-attention, input may be fed into three distinct fully connected neural network layers to create query, key, and value vectors. Query, key, and value vectors may be fed through a linear layer; then, the query and key vectors may be multiplied using dot product matrix multiplication in order to produce a score matrix. The score matrix may determine the amount of focus for a word should be put on other words (thus, each word may be a score that corresponds to other words in the time-step). The values in score matrix may be scaled down. As a non-limiting example, score matrix may be divided by the square root of the dimension of the query and key vectors. In some embodiments, the softmax of the scaled scores in score matrix may be taken. The output of this softmax function may be called the attention weights. Attention weights may be multiplied by your value vector to obtain an output vector. The output vector may then be fed through a final linear layer.

Still referencing FIG. 1, in order to use self-attention in a multi-headed attention computation, query, key, and value may be split into N vectors before applying self-attention. Each self-attention process may be called a "head." Each head may produce an output vector and each output vector from each head may be concatenated into a single vector. This single vector may then be fed through the final linear layer discussed above. In theory, each head can learn something different from the input, therefore giving the encoder model more representation power.

With continued reference to FIG. 1, encoder of transformer may include a residual connection. Residual connection may include adding the output from multi-headed attention to the positional input embedding. In some embodiments, the output from residual connection may go through a layer normalization. In some embodiments, the normalized residual output may be projected through a pointwise feed-forward network for further processing. The pointwise feed-forward network may include a couple of linear layers with a ReLU activation in between. The output may then be added to the input of the pointwise feed-forward network and further normalized.

Continuing to refer to FIG. 1, transformer architecture may include a decoder. Decoder may a multi-headed attention layer, a pointwise feed-forward layer, one or more residual connections, and layer normalization (particularly after each sub-layer), as discussed in more detail above. In some embodiments, decoder may include two multi-headed attention layers. In some embodiments, decoder may be autoregressive. For the purposes of this disclosure, "autoregressive" means that the decoder takes in a list of previous outputs as inputs along with encoder outputs containing attention information from the input.

With further reference to FIG. 1, in some embodiments, input to decoder may go through an embedding layer and positional encoding layer in order to obtain positional embeddings. Decoder may include a first multi-headed attention layer, wherein the first multi-headed attention layer may receive positional embeddings.

With continued reference to FIG. 1, first multi-headed attention layer may be configured to not condition to future tokens. As a non-limiting example, when computing attention scores on the word "am," decoder should not have access to the word "fine" in "I am fine," because that word is a future word that was generated after. The word "am" should only have access to itself and the words before it. In some embodiments, this may be accomplished by implementing a look-ahead mask. Look ahead mask is a matrix of the same dimensions as the scaled attention score matrix that is filled with "0s" and negative infinities. For example, the top right triangle portion of look-ahead mask may be filled with negative infinities. Look-ahead mask may be added to scaled attention score matrix to obtain a masked score matrix. Masked score matrix may include scaled attention scores in the lower-left triangle of the matrix and negative infinities in the upper-right triangle of the matrix. Then, when the softmax of this matrix is taken, the negative infinities will be zeroed out; this leaves zero attention scores for "future tokens."

Still referring to FIG. 1, second multi-headed attention layer may use encoder outputs as queries and keys and the outputs from the first multi-headed attention layer as values. This process matches the encoder's input to the decoder's input, allowing the decoder to decide which encoder input is relevant to put a focus on. The output from second multi-headed attention layer may be fed through a pointwise feedforward layer for further processing.

With continued reference to FIG. 1, the output of the pointwise feedforward layer may be fed through a final linear layer. This final linear layer may act as a classifier. This classifier may be as big as the number of classes that you have. For example, if you have 10,000 classes for 10,000 words, the output of that classifier will be of size 10,000. The output of this classifier may be fed into a softmax layer which may serve to produce probability scores between zero and one. The index may be taken of the highest probability score in order to determine a predicted word.

Still referring to FIG. 1, decoder may take this output and add it to the decoder inputs. Decoder may continue decoding until a token is predicted. Decoder may stop decoding once it predicts an end token.

Continuing to refer to FIG. 1, in some embodiment, decoder may be stacked N layers high, with each layer taking in inputs from the encoder and layers before it. Stacking layers may allow an LLM 132 to learn to extract and focus on different combinations of attention from its attention heads.

With continued reference to FIG. 1, an LLM 132 may receive an input. Input may include a string of one or more characters. Inputs may additionally include unstructured data. For example, input may include one or more words, a sentence, a paragraph, a thought, a query, and the like. A "query" for the purposes of the disclosure is a string of characters that poses a question. In some embodiments, input may be received from a user device. User device may be any computing device 104 that is used by a user. As non-limiting examples, user device may include desktops, laptops, smartphones, tablets, and the like. In some embodiments, input may include any set of data associated with natural language medical database query. In one or more embodiments, LLM 132 may be configured to receive natural language medical database query in order to convert natural language medical database query into machine-readable queries.

With continued reference to FIG. 1, an LLM 132 may generate at least one annotation as an output. At least one annotation may be any annotation as described herein. In some embodiments, an LLM 132 may include multiple sets of transformer architecture as described above. Output may include a textual output. A "textual output," for the purposes of this disclosure is an output comprising a string of one or more characters. Textual output may include, for example, a plurality of annotations for unstructured data. In some embodiments, textual output may include a phrase or sentence identifying the status of a user query. In some embodiments, textual output may include a sentence or plurality of sentences describing a response to a user query. As a non-limiting example, this may include restrictions, timing, advice, dangers, benefits, and the like.

With continued reference to FIG. 1, LLM 132 may receive natural language medical database query and output a computer language query 136. A "computer language query" for the purposes of this disclosure is a request for medical information in a language suitable for a computing system to process. For example, and without limitation, computer language query 136 may include a request in structured query language (SQL), in computer-generated code, GraphQL DQL, in keywords and/or any other query languages. In an embodiment, computer language query 136 may include requests made within the language of a computing system whereas natural language query 120 may include requests made in natural human language. In one or more embodiments, computer language query 136 may include a request within natural language medical database query that has been converted into a language used particularly for retrieval of information from a computing system. In an embodiment, natural language medical database query may include natural language requests whereas computer language query 136 may include requests made in computer language. In one or more embodiments, computing systems may rely on computer language to receive and process tasks wherein requests must be made in the computer language in order to properly process and generate said tasks. In an embodiment, LLM 132 may receive a request made by a user in a natural language and convert the natural language into code and/or into a query language suitable for data retrieval.

In one or more embodiments, LLM 132 may be located on a remote server, cloud network and the like. In one or more embodiments, LLM 132 may be communicatively connected to processor 108 and/or database 116. In one or more embodiments, database 116 may include information associated with medical records, such as but not limited to, electronic records as described above, electronic health records and the like. In an embodiment, LLM 132 may be configured to receive a request from a user in a natural language and convert the request into computer language in order to retrieve information from database 116.

With continued reference to FIG. 1, computer language query 136 may include a plurality of nodes 140. A "node" as referred to herein refers to an element or entity within a data structure. A node 140 in the context of database 116 queries, also referred to as a 'query generation node' may refer to a step or action in the process of generating a query. For example, and without limitation, node 140 may include a step of accessing a database 116 of files, accessing a particular classification of files and the like. In one or more embodiments nodes 140 may include steps such as, but not limited to receiving data associated with patients of a particular age, receiving data associated with patients with a particular medication condition, receiving data associated with patients using a particular medication and the like. In one or more embodiments, computer language query 136 may contain a plurality of tasks needed to process a request association with natural language medical database query wherein each task may be associated with node 140. In one or more embodiments, each node 140 may represent a specific piece of information or condition related to the request provided by the user. In one or more embodiments, nodes 140 may be used by database 116 to find and retrieve information. In one or more embodiments, nodes 140 may be specific to database 116 what information should be retrieved. In one or more embodiments, nodes 140 may include operations like table scans, index lookups, filtering conditions, and the like. In one or more embodiments, LLM 132 may be configured to generate an SQL query including a plurality of nodes 140 wherein each node 140 may refer to a specific step in a process of data retrieval. In one or more embodiments, nodes 140 are used to filter and define the cohorts of patients based on various criteria such as age, medical condition, medication and the like. In one or more embodiments, nodes 140 may provide instructions on how to identify and select the relevant data points from database 116. In one or more embodiments, nodes 140 may represent specific actions or conditions that need to be performed or met in order to retrieve the desired information from database 116 and/or the patient database 116. Each node 140 may correspond to a specific element or event mentioned in natural language query 120 and may serve as a step in the process of generating a final query as described in more detail below. In an embodiment, each node 140 may be associated with a separate query, wherein each node 140 may result in a different request received from database 116.

With continued reference to FIG. 1, LLM 132 may be configured to generate computer language query 136 by identifying one or more atomic elements 144 within natural language query 120. An "atomic element" for the purposes of this disclosure refers to the smallest unit of a query. For example, and without limitation, atomic element 144 may include a keyword, an identifier, operators and the like. In an embodiment, atomic elements 144 may indicate limitations of a query such as but not limited to, the particular row or classes of data to be searched, various conditions that must be met and the like. In one or more embodiments, atomic elements 144 are used to filter and define cohorts of patients in a query or request within natural language patient database query. In one or more embodiments, LLM 132 may be configured to segment a request within natural language query 120 into a plurality of atomic elements 144 wherein each element may be used to generate a node 140. For example, and without limitation, a request such as "give me a list of female patients with diabetes" may include atomic elements 144 such as "female," "diabetes", "with" and the like. In an embodiment atomic elements 144 may indicate events, individuals, conditions and the like to be met within a query. In one or more embodiments, atomic elements 144 may indicate an age, gender, medical condition, medical treatment and the like that must be used to generate a query. In one or more embodiments, using the example associated with female patients with diabetes, atomic elements 144 may be used to search database 116 for females, then females with diabetes. In one or more embodiments, LLM 132 may be configured to segment natural language query 120 in into a plurality of atomic elements 144 wherein each atomic element 144 may indicate a keyword, identifier, operator, literal (e.g. numbers, dates and the like) and the like. In an embodiment, LLM 132 may use one or more classification techniques in order to identify atomic elements 144 within each natural language query 120. In one or more embodiments, LLM 132 may use a classifier, such as a machine learning model in order to classify portions of natural language query 120 into various groupings. In an embodiment, each grouping may refer to a particular class of atomic elements 144, such as but not limited to keyword and/or identifier. In one or more embodiments, each atomic element 144 may be used to generate a node 140 within generate computer language query 136. For example, and without limitation, an atomic element 144 such as "female" may be used to create a node 140 to search database 116 for females. Similarly, an atomic element 144 such as "diabetes, may be used to search database 116 for patients with diabetes. In one or more embodiments, LLM 132 may be configured to identify one or more atomic elements 144 and generate a node 140 for one or more atomic elements 144.

With continued reference to FIG. 1, LLM 132 may be configured to map plurality of nodes 140 to one or more entries within database 116. 'Mapped nodes' and/or the processing of 'mapping nodes' refer to the nodes 140 generated by the LLM 132 that have been associated or linked to specific elements or entries in database 116. In one or more embodiments, mapped nodes 140 represent the different criteria or conditions specified in the natural language query 120 which have been mapped to entries in database 116. The mapping process may include identifying the relevant elements in the database 116 that correspond to each node 140 generated by the LLM 132. For example, and without limitation, a node 140 tasked with finding patients who are female may be mapped to entries indicating female patients. Mapped nodes 140 are the result of inputting a natural language medical database query into a large language model (LLM 132). The LLM 132 analyzes the query and identifies specific elements or events that are relevant to the query. These elements or events are represented as nodes 140 in the LLM 132's output. In one or more embodiments, nodes 140 represent different criteria or conditions that need to be considered when retrieving information from database 116. Each node 140 may captures a specific aspect of the query, such as time range, age, diagnosis, medication and the like. In one or more embodiments, mapping nodes 140 may allow for system and/or LLM 132 to understand what information may exist within database 116. In one or more embodiments, mapping nodes 140 may include identifying individuals, records and the like that correspond to a particular node 140. For example, and without limitation, a node 140 for finding female patients may be mapped to identified female patients. As a result, the LLM 132 may have an understanding of the amount of female patients that exist within database 116. In one or more embodiments, LLM 132 and/or system may not know what data entries may exist in database 116 and/or patient database 116 until a response is received for each node 140. In one or more embodiments, LLM 132 may generate a computer language query 136 in order to determine what entries may exist within database 116. In one or more embodiments, LLM 132 may generate a plurality of nodes 140 as a function of atomic elements 144 and map plurality of nodes 140 to entries in database 116. In one or more embodiments, LLM 132 may receive a response from database 116 indicating entries in the database 116. In one or more embodiments, LLM 132 may query database 116 using SQL queries and/or other querying languages to receive entries associated with the queries.

With continued reference to FIG. 1, in one or more embodiments, LLM 132 may be configured to receive a database response 148 as a function of the computer language query 136. A "database response" for the purposes of this disclosure is information received from database 116 based on the nodal outputs within computer language query 136. In one or more embodiments, computer language query 136 may contain a plurality of nodes 140 indicating constraints, filters, and the like wherein database response 148 may include entries from database 116 that satisfied the conditions. For example, and without limitation, a computer generated query indicating to retrieve patients who are female may result in a database response 148 indicating which entries are correlated to female patients and/or how many entries within database 116 may be associated with female patients. In one or more embodiments, database response 148 may allow for LLM 132 and/or system to understand what particular entries are located in database 116. In one or more embodiments, LLM 132 may first query database 116 to determine what entries may exist wherein LLM 132 may then query database 116 for entries associated specifically with a request within natural language query 120. In one or more embodiments, database response 148 may include entries identified as a function of each atomic element 144, each node 140 and the like. In one or more embodiments, database response 148 may include a plurality of responses wherein each response may be associated with a particular node 140, atomic element 144 and the like. For example, and without limitation, database response 148 may indicate first set of entries of patients aged 45 years or older, a second set of entries of patients diagnosed with metastatic breast cancer, a third set of entries of patients with a specific disease and the like. This node 140 is necessary to identify the specific disease condition of interest. In one or more embodiments, prior to querying a database 116 for a particular result, LLM 132 and/or processor 108 may first determine which entries first exist within database 116.

With continued reference to FIG. 1, LLM 132 may be configured to extract patient cohorts 152 for each atomic element 144 as a function of database response 148. In an embodiment, database response 148 may include a plurality of patient cohorts 152 wherein each patient cohorts 152 are associated with a particular node 140 and/or atomic element 144. A "patient cohort" for the purposes of this disclosure is a grouping of individuals with similar physical or medical attributes. For example, and without limitation, a patient cohort 152 May include a group of people are female, who are above a particular age, who have been diagnosed with a particular disease and the like. In one or more embodiments, cohorts may be used upon age, gender, medical background, medical history and the like. In one or more embodiments, processor 108 and/or LLM 132 may generate patient cohort 152 for each node 140 and/or atomic element 144. For example, and without limitation, a patient cohort 152 containing females may be created in instances in which an identified atomic element 144 includes females. In one or more embodiments, LLM 132 may identify a patient cohort 152 for each atomic element 144 wherein each patient cohort 152 may include individuals associated with the particular atomic element 144. In one or more embodiments, LLM 132 may create a node 140 for each atomic element 144 wherein each node 140 may generate a patient cohort 152 for each atomic element 144 based on database response 148. In one or more embodiments, LLM 132 may query a database 116 for patient cohorts 152 wherein LLM 132 may receive patient cohorts 152 and/or information associated with patient cohorts 152. In one or more embodiments, LLM 132 may query database 116 wherein database response 148 may contain patient cohorts 152, wherein each patient cohort 152 is identified entries associated with a particular atomic element 144 and/or node 140.

With continued reference to FIG. 1, LLM 132 may be configured to receive database response 148 to generate a final database query 156. In one or more embodiments, processor 108 and/or LLM 132 may be configured to generate final database query 156 as a function of database response 148. A "Final database query" as described in this disclosure is a request generated in a query language to receive information associated with natural language query 120 as described above. For example, and without limitation, natural language query 120 may include a request to receive information associated with patients over the age of 45 who have diabetes, wherein final database query 156 may include a request in query language to receive information associated with patients over the age of 45 from database 116 such as patient database 116. In an embodiment, computer language query 136 may be used to query patient database 116 in order to understand what information may be present within database 116 wherein final database query 156 may be used to request the particular information desired as indicated within natural language query 120. For example, and without limitation, computer language query 136 may indicate to receive a first set of information indicating identification of patients over the age of 45 and a second set of information indicating identification of patients with diabetes. Continuing, final database query 156 may indicate to receive information solely to those patients who are over age 45 and have diabetes. In an embodiment, computer language query 136 may be used to query a database 116 to identify relevant entries whereas final database query 156 may be used narrow down the entries to relevant entries.

With continued reference to FIG. 1, LLM 132 may be configured to generate a plurality of logical relationships 160 as a function of either natural language query 120 and/or database response 148. In an embodiment, generating final database response 148 may include identifying and/or generating plurality of logical relationships 160 between plurality of nodes 140 as a function of database response 148 and generating database response 148 as a function of plurality of logical relationships 160. A "logical relationship" for the purposes of this disclosure refers the connections or associations between nodes 140. For example, and without limitation, logical relationship 160 may indicate that a node 140 indicating a patients age and a node 140 indicating a patient's gender wherein both nodes 140 are associated with the physical characteristics of the patient. In another non limiting example. A logical relationship 160 may indicate that a node 140 indicating patients with metastatic breast cancer and a node 140 indicating patients taking the medication Letrozole may be related since the medication is medication needed to treat breast cancer. In one or more embodiments, logical relationships 160 may be used to filter through patient cohorts 152 received from database response 148. In one or more embodiments, logical relationships 160 may be used to narrow down particular groups of people in order to properly retrieve information associated with a request within natural language query 120. In one or more embodiments, LLM 132 may determine logical relationships 160 between nodes 140 in order to filter database 116 for only those entries that are associated with Natural language query 120. In one or more embodiments, logical relationships 160 may include, but are not limited to, associations due to physical characteristics, associations due to cause and effect, associations due to temporal effects and the like. For example, and without limitation, logical relationships 160 may include associations between age and gender to reduce the amount of determined entries in database 116. In one or more embodiments, LLM 132 may identify logical relationships 160 between nodes 140 and combine nodes 140. In one or more embodiments, Computer generated query may include multiple queries wherein each query may include a particular broad request. In an embodiment, logical relationship 160 may allow for combining queries in order to filter results. In one or more embodiments, LLM 132 may be configured to determine logical relationships 160 between nodes 140 and/or atomic elements 144 and generate final database query 156 as a result. In an embodiment, a logical relationship 160 may include that a medication and diagnoses are related, and that the medication is taken after the diagnoses. Continuing, final database query 156 may include nodes 140 indicating that both medications and the diagnoses should be found in the entry and that the diagnoses is given before the medication. In one or more embodiments, logical relationships 160 may identify and/or provide constraints to computer language query 136. For example, and without limitation, a request indicating for information of women over 45 may indicate that a constraint exists such that anyone over 45 must also be a woman. In one or more embodiments, LLM 132 may be configured to retrieve and/or identify entries associated with each atomic element 144 then filter the entries based on logical relationships 160.

With continued reference to FIG. 1, generating logical relationships 160 may include identifying temporal relationships 164. A "temporal relationship" for the purposes of this disclosure is an association between two sets of information based on a time element. For example, and without limitation, a medication and a disease might have a temporal relationship 164 wherein the medication must be given after diagnosis of the disease. As a result, a logical relationship 160 may indicate that entries first be sorted by disease then by medication. In one or more embodiments, temporal relationship 164 may further indicate that a particular procedure given may only occur following diagnosis. In another non limiting example, a temporal relationship 164 may indicate that a disease must be identified before a certain age. In one or more embodiments, LLM 132 may determine temporal relationships 164 between atomic elements 144 wherein temporal relationships 164 may indicate that one query must supersede the other. In one or more embodiments, LLM 132 may identify temporal relationships 164 in order to filter entries identified. In one or more embodiments LLM 132 may determine temporal relationships 164 between elements within natural language query 120.

With continued reference to FIG. 1, LLM 132 may be configured to generate logical nodes as a function of the logical relationships 160. A "logical node" for the purposes of this disclosure refers to the logical operations performed on data in order to achieve a desired outcome. For example, and without limitation, Logical nodes may include a process of filtering data, joining data, grouping data and the like. In one or more embodiments, logical nodes may combine one or more nodes 140 using operators such as an 'AND' operation, an 'OR' operation and the like. In embodiment, an AND operation may be used to filter results containing both sets of information such as a particular age and a gender. In one or more embodiments, logical nodes may be used to combine one or more queries into a single query. For example, computer language query 136 may contain multiple queries wherein each query may refer broadly to an atomic event, whereas logical nodes may be used to combine queries and filter results. In one or more embodiments, logical nodes may be used to satisfy constraints or conditions determined by logical relationships 160. In one or more embodiments, LLM 132 may be configured to combine queries in order to filter results. In one or more embodiments, LLM 132 may be configured to determine a logical relationship 160 between a pair of nodes 140 and create logical nodes between the pair. In one or more embodiments LLM 132 may be configured to generate relationships between nodes 140 and/or logical nodes until a single logical node may exist to generate a singly query. In one or more embodiments, the single logical node may encompass the plurality of nodes 140 and include limitations and/or restraints as indicated within logical relationships 160. In one or more embodiments, LLM 132 may be configured to generate a plurality of nodes 140 from the plurality of atomic elements 144 within natural language query 120 and combine nodes 140 until a single logical node may exists. In one or more embodiments, a non-illustrating example of this process may be described as follows below:

Natural language query: generate a cohort of female patients with age >=45 years of age diagnosed with metastatic breast cancer and on letrozole and palbociclib.

Computer Language Query:
  i. E1: Create a node for records within the last year.
  ii. E2: Create a node for patients aged 45 years or older. This node is necessary to filter the cohort by the specified age criteria.
  iii. E3: Create a node for patients diagnosed with metastatic breast cancer.
  This node is necessary to identify the specific disease condition of interest.
  iv. E4: Create a node for patients on letrozole. This node is necessary to identify patients receiving this specific medication.
  v. E5: Create a node for patients on palbociclib. This node is necessary to identify patients receiving this specific medication.

Database Response:
  i. E1: Patients with gender equal to female=3806528
  ii. E2: Patients with age equal to or grater to 45=4565986
  iii. E3: Patients with disease equal to metastatic breast cancer=16095
  iv. E4: Patients with medicine equal to letrozole=17914
  V. E5: Patients with medicine equal to palbociclib=2012
  vi.

Final Database Query:
  i. [R1]: Create a hyperLogicalNode (logical_node gender_age) by merging <node_1> and <node_2> using the AND operator. This will define a cohort of female patients who are 45 years of age or older. There is no temporal relation between gender and age, so none is specified.
  ii. [R2]: Create a hyperLogicalNode (logical_node_cancer_med1) by merging <node_3> and <node_4> using the AND operator. This will define a cohort of patients diagnosed with metastatic breast cancer and on letrozole. There is an implied temporal relation that the diagnosis of cancer typically precedes the prescription of medication, but since the exact timing is not specified, we will not include a temporal relation.

iii. [R3]: Create a hyperLogicalNode (logical_node_cancer_med2) by merging <node_3> and <node_5> using the AND operator. This will define a cohort of patients diagnosed with metastatic breast cancer and on palbociclib. Similar to the previous step, there is an implied temporal relation that the diagnosis precedes the prescription, but without specific timing, we will not include a temporal relation.

iv. [R4]: Create a hyperLogicalNode (logical_node_med_combo) by merging <logical_node_cancer_med1> and <logical_node cancer_med2> using the AND operator. This will define a cohort of patients diagnosed with metastatic breast cancer who are on both letrozole and palbociclib. There is no temporal relation specified between taking letrozole and palbociclib, so none is specified.

As described above in the non-illustrative example, natural language query 120 may include a request by a user to receive information. LLM 132 may generate computer language query 136 in order to query a database 116 based on each identified atomic elements 144. In this instances, an atomic element 144 was identified to be female wherein database 116 retrieved 3,806,528 entries equal to female. In one or more embodiments, LLM 132 may then combine queries and/or nodes 140 within computer language query 136 in order to create singular query in order to retrieve information associated with the patient request.

With continued reference to FIG. 1, LLM 132 may be configured to generate final database query 156 wherein final database query 156 may include a plurality of operators indicating relationships between queries and nodes 140. In one or more embodiments, logical nodes may be used to manipulate the results of multiple queries in order to receive a single set of information corresponding to natural language query 120.

With continued reference to FIG. 1, LLM 132 is configured to query patient database 116 using final database query 156. In one or more embodiments, LLM 132 may transmit final database query 156 to database 116.

With continued reference to FIG. 1, LLM 132 may receive a user response 168 as a function of the final database query 156. A "user response" for the purposes of this disclosure is identified entries within database 116 corresponding to a request within natural, language query. For example, and without limitation, user response 168 may include entries in patient database 116 corresponding to patients over the age of 45 in instances in which natural language query 120 contains a request for patients over the age of 45. In one or more embodiments, user response 168 may include information within patient database 116 that has been associated with a request within natural language query 120. In one or more embodiments, User response 168 may include entries identified within patient database 116 as a result of a transmission of final database query 156. In one or more embodiments, user response 168 may be transmitted to a remote device associated with user. In one or more embodiments, user response 168 may be transmitted and/or communicated through a chatbot. In one or more embodiments, processor 108 may be configured to compilate identified entries within a single file and transmit the single file to user. In one or more embodiments, processor 108 may be configured to populate a spreadsheet with values associated with the entries from database 116, such as but not limited to, patient name, age, ECG signal information, diagnosis, treatment and the like.

With continued reference to FIG. 1, LLM 132 may be configured to generate a natural language response 172 as a function of user response 168. "Natural language response" for the purposes of this disclosure is user response 168 presented a natural language format. For example, and without limitation, user response 168 may include entries within database 116, feedback from the search query and the like wherein natural language response 172 may include a communication with user indicating the information contained within user response 168. In one or more embodiments, LLM 132 may be configured to summarize and/or provide information about user response 168. In one or more embodiments, natural language response 172 may include analyzation of user response 168 wherein natural language response 172 may present information contained within user response 168 to a user similar to that of an ordinary human conversation. For example and without limitation, user response 168 may include information associated with 100 data entries wherein natural language response 172 may contain a communication stating "I have found 100 patients with the results, you have provided. Would you like to me to describe the entries, or would you like to narrow further." In one or more embodiments, natural language response 172 may convert information contained within user response 168 into a format suitable for a user to understand and/or comprehend. In one or more embodiments, natural language response 172 may include follow up questions requesting whether the user would like to refine the results further or to broaden up the search. In one or more embodiments, LLM 132 may translate complex datasets from user response 168 into communication that may be made to user in the form of sentences describing user response 168. In one or more embodiments, Natural language response 172 may be in the form of human communication wherein user may communicate with chatbot system 128 and receive responses in the form of human communication.

With continued reference to FIG. 1, natural language response 172 and/or user response 168 may be generated using retrieval augmented generation. "Retrieval augmented generation (RAG)" for the purposes of this disclosure is a process in which data from external sources is used to generate a response by the large language model. For example, and without limitation, an LLM may be configured to retrieve information from a database, such as patient database wherein the response generated by the LLM may be based off of information retrieved from the database. In one or more embodiments, RAG may include retrieving information from external sources such as patient database and generating outputs such as user response 168, natural language response and/or final database query 156. In one or more embodiments, RAG may include a process fo querying database to retrieve relevant information associated with inputs and then using results in order to generate final database query 156. In embodiment, computer language query 136 may allow for an initial search of database wherein final database query may be used to find particular data elements within database 116. In one or more embodiments, RAG may include the use of leveraging external sources such as database in order to generate final database query 156. In one or more embodiments, an initial set of data may first be received by LLM in the form of database response 148 wherein information within database response 148 may be used to generate final database query 156 and the resulting user response 168 and/or natural language response 172. In one or more embodiments, processor 108 and/or LLM may be configured to search database using a query such as computer language query 136. In one or more embodiments, LLM and/or processor may be configured to retrieve relevant information from database 116 in the form of database response 148. In one or more embodiments database response 148 may be used to generate final database query 154. In one or more embodiments, user response 168 may be used to generate natural language query wherein LLM may leverage information contained within user response 168 to address a request and/or input made by user. In one or more embodiments, LLM and/or processor may use RAG to retrieve relevant information from database 116 and respond to a request using the relevant information from database. In one or more embodiments, user response 168 may be used to add additional context and/or specific context to general outputs generated by LLM. In one or more embodiments, RAG may allow for processor 108 and/or LLM to generate outputs even in instances in which the LLM may not have internal data to support the output. In one or more embodiments, RAG may be used to generate responses from non-authoritative sources, and/or to utilize terminology within external sources to provide more accurate outputs. In one or more embodiments, Natural language response 172 may include a response from LLM wherein the response is supplemented with information retrieved from user response 168.

With continued reference to FIG. 1, Natural language response 172 may be generated as a function of user profile 176. A "User profile" for the purposes of this disclosure is information associated with user. For example, and without limitation, user profile 176 may include a name, an age, a gender, professional background and the like. In one or more embodiments, user profile 176 may include a user's educational background, a user's professional background (e.g. doctor, lawyer, nurse, physician assistant and the like) and the like. In one or more embodiments, user profile 176 may include the entity or business in which the user is employed to. In one or more embodiments, user profile 176 may include information associated with previous interactions with system 100. For example, and without limitation, user profile 176 may include previously received natural language queries and/or any user inputs 124 received by system. In one or more embodiments, previous user inputs 124 may be used to train LLM 132 to output data that is personalized to user. For example, and without limitation, LLM 132 may be configured to use simpler words or more complex words based on a user's interaction with system. Similarly, LLM 132 may be configured output desired languages based on previous languages used by a user. In one or more embodiments, LLM 132 and/or processor 108 may classify natural language queries and/or user profile into one or more language groupings. A "language grouping" for the purposes of this disclosure is a label used to indicate a particular language and the complexity of the language used. For example, and without limitation, language grouping may include 'beginner English' wherein a phrase may be classified as a phrase generated in English wherein the individual's complexity of the language may be labeled as 'beginner'. Language groupings are described in further detail below. A "classifier," as used in this disclosure is a machine-learning model, such as a mathematical model, neural net, or program generated by a machine learning algorithm known as a "classification algorithm," as described in further detail below, that sorts inputs into categories or bins of data, outputting the categories or bins of data and/or labels associated therewith. Classifiers as described throughout this disclosure may be configured to output at least a datum that labels or otherwise identifies a set of data that are clustered together, found to be close under a distance metric as described below, or the like.

With continued reference to FIG. 1, processor 108 may be configured to generate classifiers as described throughout this disclosure using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database 116 116, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process for the purposes of this disclosure. As a non-limiting example, an initial heuristic may include a ranking of associations between inputs and elements of training data. Heuristic may include selecting some number of highest-ranking associations and/or training data elements.

With continued reference to FIG. 1, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors for the purposes of this disclosure may be scaled, such that each vector represents each attribute along an equivalent scale of values. Each vector may be "normalized," or divided by a "length" attribute, such as a length attribute l as derived using a Pythagorean norm:

$$l = \sqrt{\sum_{i=0}^{n} a_i^2},$$

where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With continued reference to FIG. 1, processor 108 and/or LLM 132 may be configured to classify previous user inputs 124, natural language queries and the like as described in this disclosure to one or more language groupings. In one or more embodiments, language groupings may include groupings and/or labels categorizing previous inputs based on the language received and the complexity of the language. For example, and without limitation, language groupings may include but are not limited to, beginner English, intermediate English, complex English, beginner Spanish, intermediate Spanish, beginner Farsi, intermediate Farsi and the like. In one or more embodiments, language groupings may indicate a user's use of a particular language during user inputs 124 and their proficiency in said language. For example, and without limitation, user inputs 124 may be classified to beginner English wherein processor 108 and/or LLM 132 may determine that based on the user's inputs, the user has a basic English understand. In one or more embodiments, language groupings may include language subgroupings wherein the subgroupings may indicate the proficiency of a language with respect to a particular professional field. For example, and without limitation, it may be the case that a user understand English fluently with respect to medical terminology yet has a basic understanding in general. This may be the case, for example, in instances in which the user is not a native born speaker yet attended an English speaking medical school. In one or more embodiments LLM 132 and/or processor 108 may classify natural language query 120 and/or any other user input 124 as described in this disclosure to one or more language groupings wherein outputs of LLM 132 and/or system may be generated based on the classification. In one or more embodiments, natural language response 172 may be generated as a function of the classification wherein the use of a particular language and/or complexity of the particular language may be used for natural language query 120. In one or more embodiments, natural language queries may contain a mixture of multiple complexities in instances in which a user may understand complex terms with respect to a particular field, yet only has an intermediate understanding in general. For example, and without limitation, natural language response 172 may include words or phrases that an individual with intermediate knowledge of English may understand yet contain complex words or phrases with respect to medical terms within the same response. In one or more embodiments, Natural language response 172 may include code-mixed expressions. A "Code mixed expression" for the purposes of this disclosure is a phrase, conversation or utterance that mixes two or more language dialects. For example, and without limitation, A phrase may be generated in English with Spanish phrases such as "15 patients have been found with la diabetes tipo." In one or more embodiments, Natural language response 172 may include a code-mixed expression wherein more than one language dialects are used in a phrase. In one or more embodiments, natural language response 172 may combine language complexities wherein particular words and/or categories of words may be understood by a user while others are not. In one or more embodiments, Processor 108 and/or LLM 132 may be configured to generate natural language response 172 as a function of user profile 176 wherein responses may be made with words or phrases understood by user. In one or more embodiments, processor 108 and/or LLM 132 may generate a language complexity score as a function of the classification wherein the language complexity score may include a numerical score indicating the user's understanding of a particular language. In one or more embodiments, language complexity score may be categorized by professional fields and/or terminology such as but not limited to, medical, law, engineering and the like.

With continued reference to FIG. 1, processor 108 and/or LLM 132 may receive previous use inputs and/or natural language queries and determine a user's understanding of a particular language based on the complexity of words used, the grammar involved in the user inputs 124 and the like. In one or more embodiments, language complexity may be determined based on user's interaction with chatbot system 128, system 100 and/or LLM 132 wherein phrases such as "please explain," "I Don't understand what that means," and the like may be used to indicate a user's understanding of a particular language. In one or more embodiments, processor 108 and/or LLM 132 may be iteratively trained to understand a user's language complexity wherein following each iteration a user's language complexity may increase or decrease based on previous conversations.

With continued reference to FIG. 1, processor 108 may be configured to transmit user response 168 and/or natural language response 172 to a user interface such as graphical user interface. In one or more embodiments, processor 108 may be configured to create a user interface data structure 180 as a function of at least user response 168 and/or language response. As used in this disclosure, "user interface data structure" is a data structure representing a specialized formatting of data on a computer configured such that the information can be effectively presented for a user interface. User interface data structure 180 may include any information as described in this disclosure, such as but not limited to natural language response 172, user response 168 and the like.

With continued reference to FIG. 1, processor 108 may be configured to transmit the user interface data structure 180 to a graphical user interface. Transmitting may include, and without limitation, transmitting using a wired or wireless connection, direct, or indirect, and between two or more components, circuits, devices, systems, and the like, which allows for reception and/or transmittance of data and/or signal(s) therebetween. Data and/or signals therebetween may include, without limitation, electrical, electromagnetic, magnetic, video, audio, radio, and microwave data and/or signals, combinations thereof, and the like, among others. Processor 108 may transmit the data described above to database 116 wherein the data may be accessed from database 116. Processor 108 may further transmit the data above to a device display or another computing device 104. In one or more embodiments, transformations, modifications and the like made to whole slide image and/or digital slide may be placed within user interface data structure 180 in order to be visualized through a user interface.

With continued reference to FIG. 1, system may include a graphical user interface (GUI 184). For the purposes of this disclosure, a "user interface" is a means by which a user and a computer system interact. For example, through the use of input devices and software. In some cases, processor 108 may be configured to modify GUI 184 as a function of at least user response 168 and/or natural language response 172 and visually present the data through GUI 184. A user interface may include graphical user interface, command line interface (CLI), menu-driven user interface, touch user interface, voice user interface (VUI), form-based user interface, any combination thereof and the like. In some embodiments, a user may interact with the user interface using a computing device 104 distinct from and communicatively connected to processor 108. For example, a smart phone, smart tablet, or laptop operated by the user and/or participant. A user interface may include one or more graphical locator and/or cursor facilities allowing a user to interact with graphical models and/or combinations thereof, for instance using a touchscreen, touchpad, mouse, keyboard, and/or other manual data entry device. A "graphical user interface," as used herein, is a user interface that allows users to interact with electronic devices through visual representations. In some embodiments, GUI 184 may include icons, menus, other visual indicators, or representations (graphics), audio indicators such as primary notation, and display information and related user controls. A menu may contain a list of choices and may allow users to select one from them. A menu bar may be displayed horizontally across the screen such as pull-down menu. When any option is clicked in this menu, then the pull-down menu may appear. A menu may include a context menu that appears only when the user performs a specific action. An example of this is pressing the right mouse button. When this is done, a menu may appear under the cursor. Files, programs, web pages and the like may be represented using a small picture in graphical user interface. Persons skilled in the art, upon reviewing the entirety of this disclosure, will be aware of various ways in which a graphical user interface and/or elements thereof may be implemented and/or used as described in this disclosure.

With continued reference to FIG. 1, GUI 184 may contain one or more interactive elements. An "interactive element" for the purposes of this disclosure is an element within a graphical user interface that allows for communication with system 100 by a user. For example, and without limitation, interactive elements may include push buttons wherein selection of a push button, such as for example, by using a mouse, may indicate to system to perform a particular function and display the result through graphical user interface. In one or more embodiments, interactive element may include push buttons on GUI 184, wherein the selection of a particular push button may result in a particular function. In one or more embodiments, interactive elements may include words, phrases, illustrations and the like to indicate the particular process the user would like system to perform. In one or more embodiments, interaction with interactive elements may result in the display of user response 168 and/or natural language response 172. In one or more embodiments, GUI 184 may be configured to visualize differing portions of user response 168 wherein interactive element may be configured to allow for viewing of a particular portion of user response 168. In one or more embodiments, user interactions with system and/or GUI 184 may be recorded and used to provide better suited natural language responses 172. For example, and without limitation, long pauses may indicate that a user may find it difficult to understand natural language response 172 wherein LLM 132 may be configured to create simpler responses in the future.

With continued reference to FIG. 1, system 100 may further include a display device 188 communicatively connected to at least a processor 108. "Display device" for the purposes of this disclosure is a device configured to show visual information. In some cases, display device 188 may include a liquid crystal display (LCD), a cathode ray tube (CRT), a plasma display, a light emitting diode (LED) display, and any combinations thereof. Display device may include, but is not limited to, a smartphone, tablet, laptop, monitor, tablet, and the like. Display device may include a separate device that includes a transparent screen configured to display computer generated images and/or information. In some cases, display device 188 may be configured to visually present one or more data through GUI 184 to a user, wherein a user may interact with the data through GUI 184. In some cases, a user may view GUI 184 through display device 188. In one or more embodiments display device 188 may be located on remote device wherein a user may access natural language response 172 and/or user response 168 through remove device.

With continued reference to FIG. 1, processor 108 may be configured to display use response and/or natural language response 172 through GUI 184 as a function of the user interface data structure 180. In one or more embodiments, processor 108 may be configured to graphically display natural language response 172 through graphical user interface. For the purposes of this disclosure, data that is "graphically displayed" refers to data presented in a graphical format. A "graphical format" for the purposes of this disclosure is a visual representation of textual information. For example, and without limitation, textual information such as numerical values may be plotted on an X-Y chart in order to show data within a graphical format. In one or more embodiments, graphical format mat may allow for visualization of textual data such as natural language response 172 and/or user response 168 in order to view user response 168 through graphical user interface. In one or more embodiments, graphical format may include X-Y charts, heat maps and the like showing similarities between entries and/or patients within database 116. In one or more embodiments, user response 168 may be visualized through an X-Y chart wherein data may be mapped over a given period of time.

Figure 2:
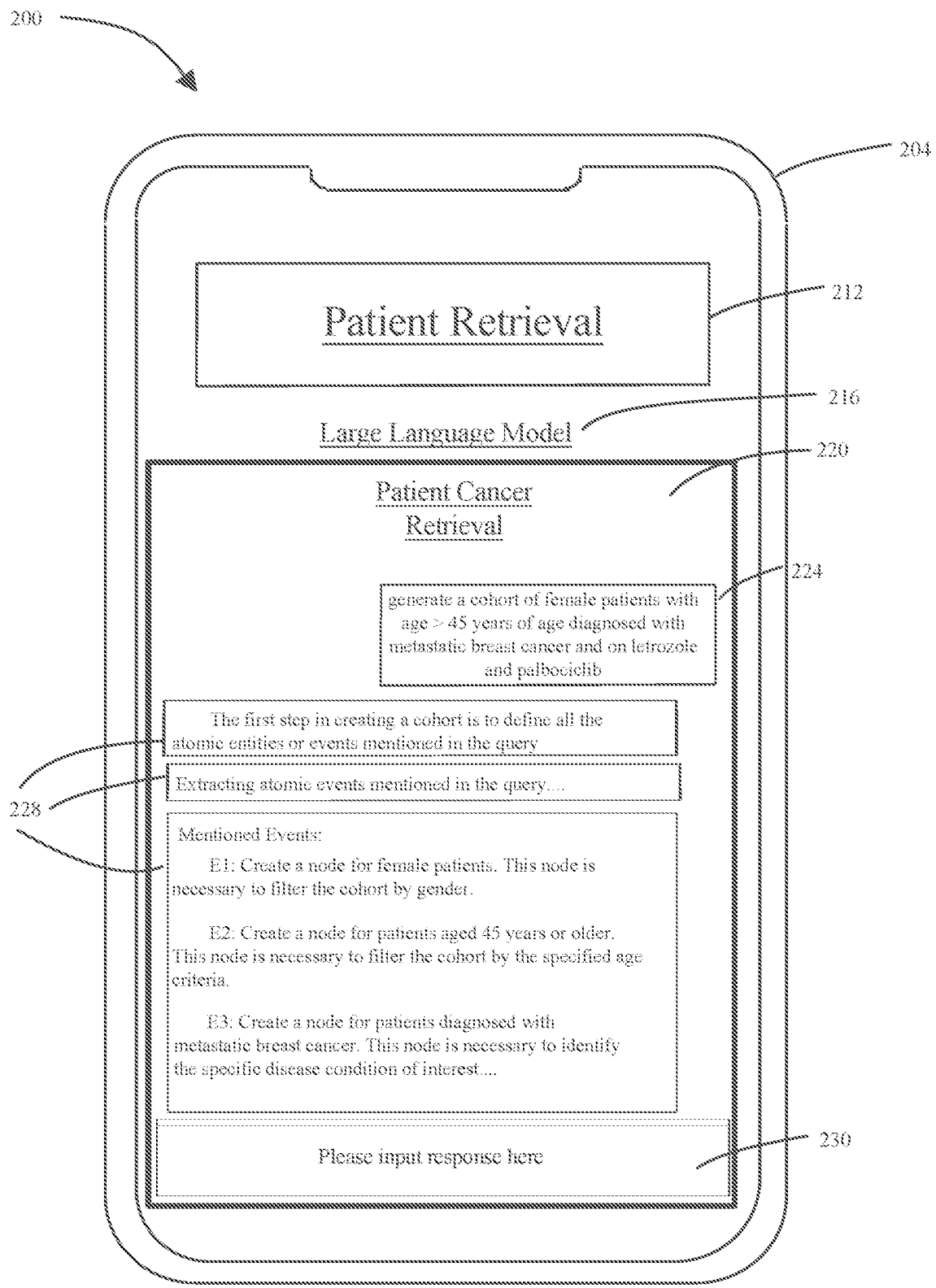
FIG. 2 illustrates an exemplary embodiment of a graphical user interface in accordance with the subject disclosure.

Referring now to FIG. 2, an exemplary embodiment of a graphical user interface 200 is described. In one or more embodiments, graphical user interface 200 (GUI) may include any GUI 200 as described in this disclosure. In one or more embodiments, GUI 200 may be configured to display information, such as atomic elements, user response, natural language query and the like (as described in reference to FIG. 1) in a graphical format. In one or more embodiments, GUI 200 may be displayed on a display device 204. In one or more embodiments, GUI may include a heading window 212 indicating the type of system that is currently being operated. In this instance, heading window may state "Patient retrieval" wherein one may be put on notice that the current system is for retrieving information associated with patients. In one or more embodiments, GUI 200 may contain a subheading 216 wherein the subheading may indicate how the data is being received, displayed, manipulated and the like. In this instance, subheading may indicate "large language model" wherein a user may be put on notice that they are interacting with a large language model. In one o more embodiments, large language model may be configured similar to a chatbot system as described in this disclosure wherein a user may interact with large language model similar to a chatbot. In one or more embodiments, GUI may contain a title 220 wherein the title 220 may indicate the type of data being received or manipulated. In this instance, title 220 may state "patient cancer retrieval" wherein a user may be put on notice that information associated with cancer patients is being retrieved. In one or more embodiments, title 220 may be generated based on user input 224 wherein the contents of user input may be used to create title 220. In one or more embodiments, user input 224 may include inputs such as natural language query as described above wherein a user may input the type of data desired. In one or more embodiments, GUI 200 may be configured to display outputs 228 of large language model, wherein outputs 228 may include outputs such as computer language query, natural language response, atomic elements and the like. In one or more embodiments, user inputs 224 may be received through a textbox feature 230 wherein the textbox feature may allow for prompts such as user inputs 224 to be entered.

Figure 3:
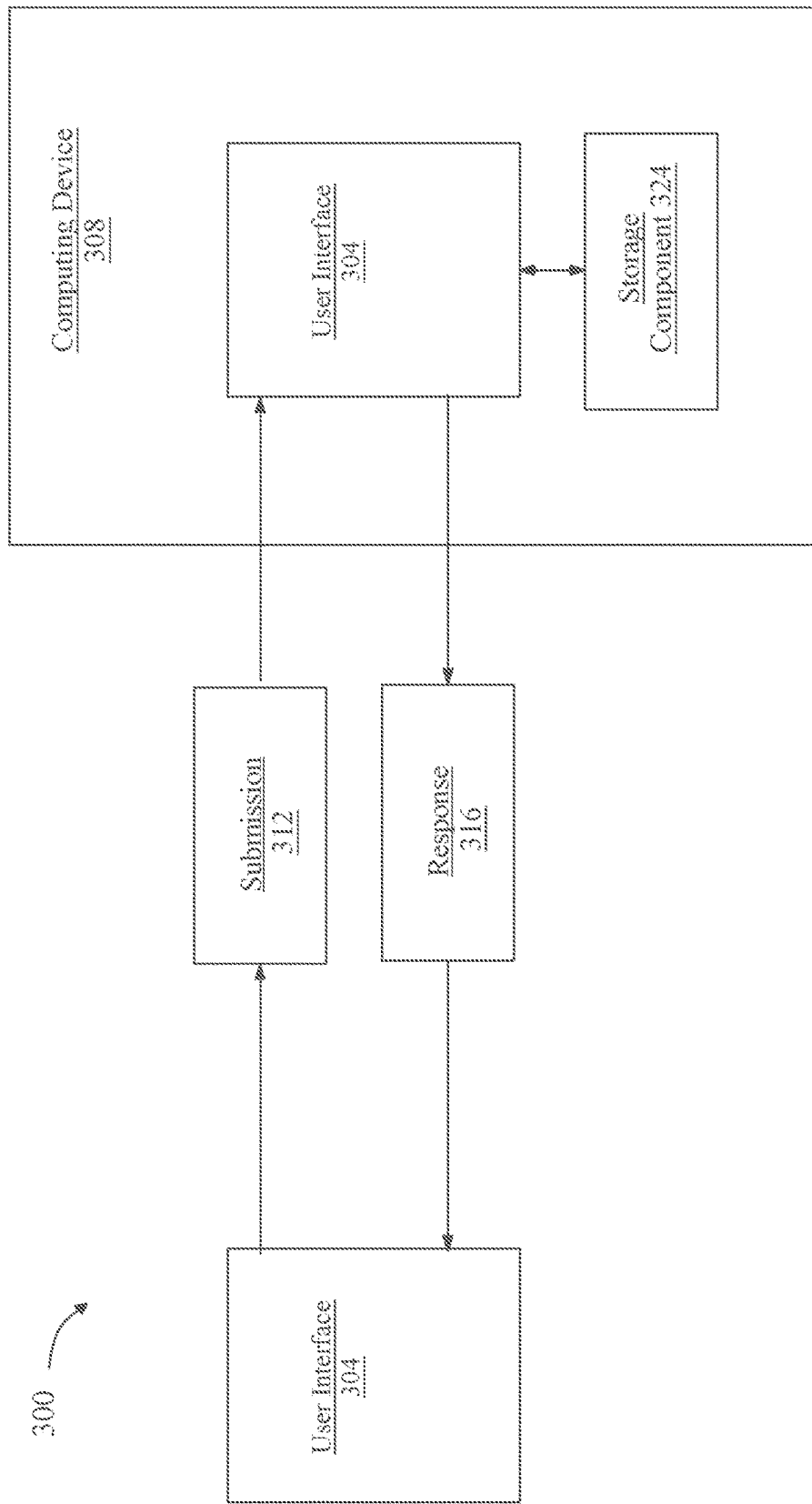
FIG. 3 illustrates is an exemplary embodiment of a chatbot system.

Referring to FIG. 3, a chatbot system 300 is schematically illustrated. According to some embodiments, a user interface 304 may be communicative with a computing device 308 that is configured to operate a chatbot. In some cases, user interface 304 may be local to computing device 308. Alternatively or additionally, in some cases, user interface 304 may remote to computing device 308 and communicative with the computing device 308, by way of one or more networks, such as without limitation the internet. Alternatively or additionally, user interface 304 may communicate with user device 308 using telephonic devices and networks, such as without limitation fax machines, short message service (SMS), or multimedia message service (MMS). Commonly, user interface 304 communicates with computing device 308 using text-based communication, for example without limitation using a character encoding protocol, such as American Standard for Information Interchange (ASCII). Typically, a user interface 304 conversationally interfaces a chatbot, by way of at least a submission 312, from the user interface 308 to the chatbot, and a response 316, from the chatbot to the user interface 304. In many cases, one or both of submission 312 and response 316 are text-based communication. Alternatively or additionally, in some cases, one or both of submission 312 and response 316 are audio-based communication.

Continuing in reference to FIG. 3, a submission 312 once received by computing device 308 operating a chatbot, may be processed by a processor 320. In some embodiments, processor 320 processes a submission 312 using one or more of keyword recognition, pattern matching, and natural language processing. In some embodiments, processor employs real-time learning with evolutionary algorithms. In some cases, processor 320 may retrieve a pre-prepared response from at least a storage component 324, based upon submission 312. Alternatively or additionally, in some embodiments, processor 320 communicates a response 316 without first receiving a submission 312, thereby initiating conversation. In some cases, processor 320 communicates an inquiry to user interface 304; and the processor is configured to process an answer to the inquiry in a following submission 312 from the user interface 304. In some cases, an answer to an inquiry present within a submission 312 from a user device 304 may be used by computing device 104 as an input to another function.

Figure 4:
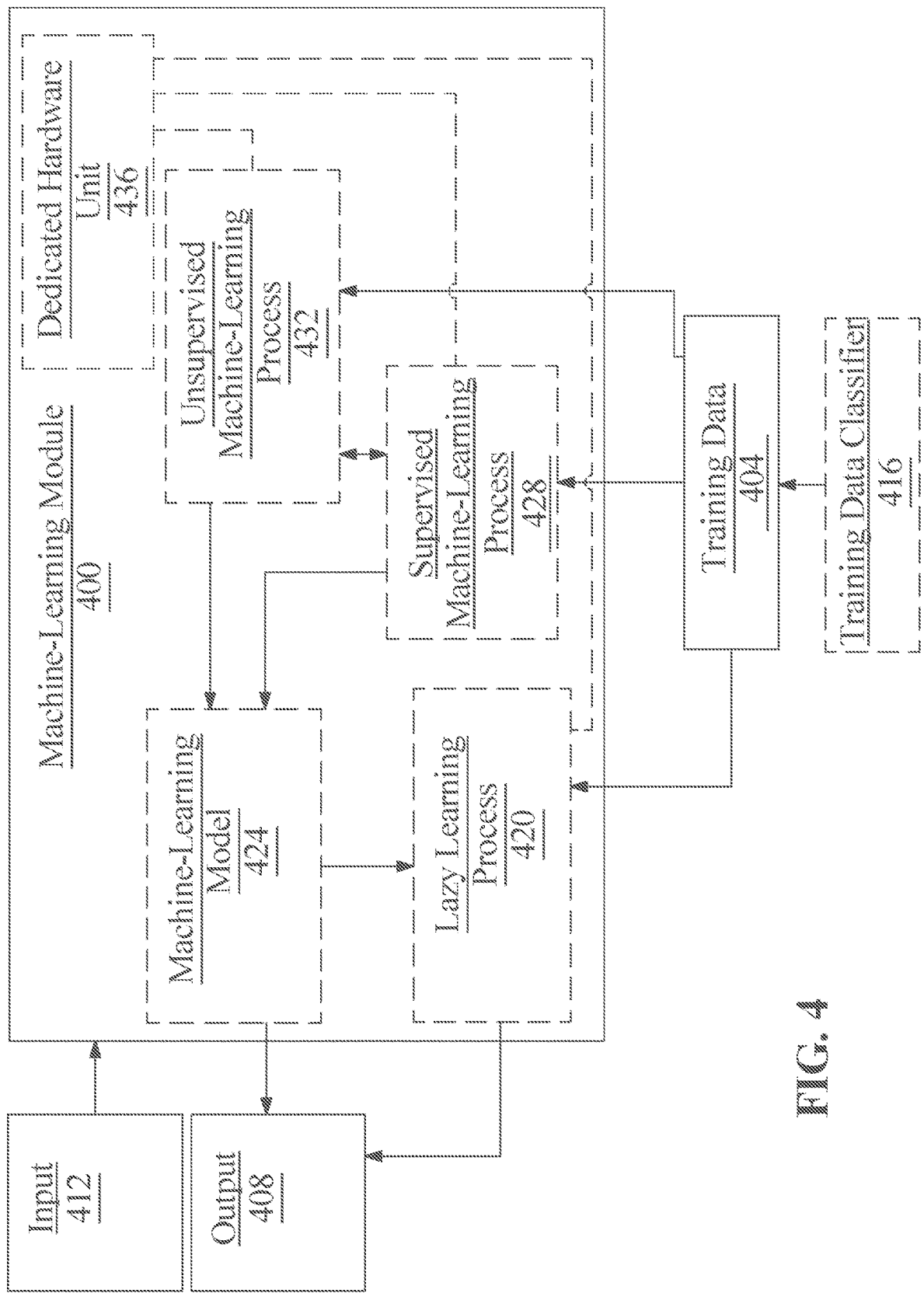
FIG. 4 is a block diagram of an exemplary machine-learning process.

Referring now to FIG. 4, an exemplary embodiment of a machine-learning module 400 that may perform one or more machine-learning processes as described in this disclosure is illustrated. Machine-learning module may perform determinations, classification, and/or analysis steps, methods, processes, or the like as described in this disclosure using machine learning processes. A "machine learning process," as used in this disclosure, is a process that automatedly uses training data 404 to generate an algorithm instantiated in hardware or software logic, data structures, and/or functions that will be performed by a computing device/module to produce outputs 408 given data provided as inputs 412; this is in contrast to a non-machine learning software program where the commands to be executed are determined in advance by a user and written in a programming language.

Still referring to FIG. 4, "training data," as used herein, is data containing correlations that a machine-learning process may use to model relationships between two or more categories of data elements. For instance, and without limitation, training data 404 may include a plurality of data entries, also known as "training examples," each entry representing a set of data elements that were recorded, received, and/or generated together; data elements may be correlated by shared existence in a given data entry, by proximity in a given data entry, or the like. Multiple data entries in training data 404 may evince one or more trends in correlations between categories of data elements; for instance, and without limitation, a higher value of a first data element belonging to a first category of data element may tend to correlate to a higher value of a second data element belonging to a second category of data element, indicating a possible proportional or other mathematical relationship linking values belonging to the two categories. Multiple categories of data elements may be related in training data 404 according to various correlations; correlations may indicate causative and/or predictive links between categories of data elements, which may be modeled as relationships such as mathematical relationships by machine-learning processes as described in further detail below. Training data 404 may be formatted and/or organized by categories of data elements, for instance by associating data elements with one or more descriptors corresponding to categories of data elements. As a non-limiting example, training data 404 may include data entered in standardized forms by persons or processes, such that entry of a given data element in a given field in a form may be mapped to one or more descriptors of categories. Elements in training data 404 may be linked to descriptors of categories by tags, tokens, or other data elements; for instance, and without limitation, training data 404 may be provided in fixed-length formats, formats linking positions of data to categories such as comma-separated value (CSV) formats and/or self-describing formats such as extensible markup language (XML), JavaScript Object Notation (JSON), or the like, enabling processes or devices to detect categories of data.

Alternatively or additionally, and continuing to refer to FIG. 4, training data 404 may include one or more elements that are not categorized; that is, training data 404 may not be formatted or contain descriptors for some elements of data. Machine-learning algorithms and/or other processes may sort training data 404 according to one or more categorizations using, for instance, natural language processing algorithms, tokenization, detection of correlated values in raw data and the like; categories may be generated using correlation and/or other processing algorithms. As a non-limiting example, in a corpus of text, phrases making up a number "n" of compound words, such as nouns modified by other nouns, may be identified according to a statistically significant prevalence of n-grams containing such words in a particular order; such an n-gram may be categorized as an element of language such as a "word" to be tracked similarly to single words, generating a new category as a result of statistical analysis. Similarly, in a data entry including some textual data, a person's name may be identified by reference to a list, dictionary, or other compendium of terms, permitting ad-hoc categorization by machine-learning algorithms, and/or automated association of data in the data entry with descriptors or into a given format. The ability to categorize data entries automatedly may enable the same training data 404 to be made applicable for two or more distinct machine-learning algorithms as described in further detail below. Training data 404 used by machine-learning module 400 may correlate any input data as described in this disclosure to any output data as described in this disclosure. As a non-limiting illustrative example inputs may include inputs such as database responses, user profiles and/or any other inputs as described above wherein outputs may include outputs such as language groupings, final database queries and the like.

Further referring to FIG. 4, training data may be filtered, sorted, and/or selected using one or more supervised and/or unsupervised machine-learning processes and/or models as described in further detail below; such models may include without limitation a training data classifier 416. Training data classifier 416 may include a "classifier," which as used in this disclosure is a machine-learning model as defined below, such as a data structure representing and/or using a mathematical model, neural net, or program generated by a machine learning algorithm known as a "classification algorithm," as described in further detail below, that sorts inputs into categories or bins of data, outputting the categories or bins of data and/or labels associated therewith. A classifier may be configured to output at least a datum that labels or otherwise identifies a set of data that are clustered together, found to be close under a distance metric as described below, or the like. A distance metric may include any norm, such as, without limitation, a Pythagorean norm. Machine-learning module 400 may generate a classifier using a classification algorithm, defined as a processes whereby a computing device and/or any module and/or component operating thereon derives a classifier from training data 404. Classification may be performed using, without limitation, linear classifiers such as without limitation logistic regression and/or naive Bayes classifiers, nearest neighbor classifiers such as k-nearest neighbors classifiers, support vector machines, least squares support vector machines, fisher's linear discriminant, quadratic classifiers, decision trees, boosted trees, random forest classifiers, learning vector quantization, and/or neural network-based classifiers. As a non-limiting example, training data classifier 416 may classify elements of training data to languages first then language complexity. In an embodiments, a language may first be identified within a natural language query wherein a complexity may then be determined, Still referring to FIG. 4, computing device 404 may be configured to generate a classifier using a Naïve Bayes classification algorithm. Naïve Bayes classification algorithm generates classifiers by assigning class labels to problem instances, represented as vectors of element values. Class labels are drawn from a finite set. Naïve Bayes classification algorithm may include generating a family of algorithms that assume that the value of a particular element is independent of the value of any other element, given a class variable. Naïve Bayes classification algorithm may be based on Bayes Theorem expressed as $P(A/B)=P(B/A) P(A)\div P(B)$, where $P(A/B)$ is the probability of hypothesis A given data B also known as posterior probability; $P(B/A)$ is the probability of data B given that the hypothesis A was true; $P(A)$ is the probability of hypothesis A being true regardless of data also known as prior probability of A; and $P(B)$ is the probability of the data regardless of the hypothesis. A naïve Bayes algorithm may be generated by first transforming training data into a frequency table. Computing device 404 may then calculate a likelihood table by calculating probabilities of different data entries and classification labels. Computing device 404 may utilize a naïve Bayes equation to calculate a posterior probability for each class. A class containing the highest posterior probability is the outcome of prediction. Naïve Bayes classification algorithm may include a gaussian model that follows a normal distribution. Naïve Bayes classification algorithm may include a multinomial model that is used for discrete counts. Naïve Bayes classification algorithm may include a Bernoulli model that may be utilized when vectors are binary.

With continued reference to FIG. 4, computing device 404 may be configured to generate a classifier using a K-nearest neighbors (KNN) algorithm. A "K-nearest neighbors algorithm" as used in this disclosure, includes a classification method that utilizes feature similarity to analyze how closely out-of-sample-features resemble training data to classify input data to one or more clusters and/or categories of features as represented in training data; this may be performed by representing both training data and input data in vector forms, and using one or more measures of vector similarity to identify classifications within training data, and to determine a classification of input data. K-nearest neighbors algorithm may include specifying a K-value, or a number directing the classifier to select the k most similar entries training data to a given sample, determining the most common classifier of the entries in the database, and classifying the known sample; this may be performed recursively and/or iteratively to generate a classifier that may be used to classify input data as further samples. For instance, an initial set of samples may be performed to cover an initial heuristic and/or "first guess" at an output and/or relationship, which may be seeded, without limitation, using expert input received according to any process as described herein. As a non-limiting example, an initial heuristic may include a ranking of associations between inputs and elements of training data. Heuristic may include selecting some number of highest-ranking associations and/or training data elements.

With continued reference to FIG. 4, generating k-nearest neighbors algorithm may generate a first vector output containing a data entry cluster, generating a second vector output containing an input data, and calculate the distance between the first vector output and the second vector output using any suitable norm such as cosine similarity, Euclidean distance measurement, or the like. Each vector output may be represented, without limitation, as an n-tuple of values, where n is at least two values. Each value of n-tuple of values may represent a measurement or other quantitative value associated with a given category of data, or attribute, examples of which are provided in further detail below; a vector may be represented, without limitation, in n-dimensional space using an axis per category of value represented in n-tuple of values, such that a vector has a geometric direction characterizing the relative quantities of attributes in the n-tuple as compared to each other. Two vectors may be considered equivalent where their directions, and/or the relative quantities of values within each vector as compared to each other, are the same; thus, as a non-limiting example, a vector represented as [5, 10, 15] may be treated as equivalent, for purposes of this disclosure, as a vector represented as [1, 2, 3]. Vectors may be more similar where their directions are more similar, and more different where their directions are more divergent; however, vector similarity may alternatively or additionally be determined using averages of similarities between like attributes, or any other measure of similarity suitable for any n-tuple of values, or aggregation of numerical similarity measures for the purposes of loss functions as described in further detail below. Any vectors as described herein may be scaled, such that each vector represents each attribute along an equivalent scale of values. Each vector may be "normalized," or divided by a "length" attribute, such as a length attribute/as derived using a Pythagorean norm: $l=\sqrt{\sum_{i=0}^{n} a_i^2}$, where $a_i$ is attribute number i of the vector. Scaling and/or normalization may function to make vector comparison independent of absolute quantities of attributes, while preserving any dependency on similarity of attributes; this may, for instance, be advantageous where cases represented in training data are represented by different quantities of samples, which may result in proportionally equivalent vectors with divergent values.

With further reference to FIG. 4, training examples for use as training data may be selected from a population of potential examples according to cohorts relevant to an analytical problem to be solved, a classification task, or the like. Alternatively or additionally, training data may be selected to span a set of likely circumstances or inputs for a machine-learning model and/or process to encounter when deployed. For instance, and without limitation, for each category of input data to a machine-learning process or model that may exist in a range of values in a population of phenomena such as images, user data, process data, physical data, or the like, a computing device, processor, and/or machine-learning model may select training examples representing each possible value on such a range and/or a representative sample of values on such a range. Selection of a representative sample may include selection of training examples in proportions matching a statistically determined and/or predicted distribution of such values according to relative frequency, such that, for instance, values encountered more frequently in a population of data so analyzed are represented by more training examples than values that are encountered less frequently. Alternatively or additionally, a set of training examples may be compared to a collection of representative values in a database and/or presented to a user, so that a process can detect, automatically or via user input, one or more values that are not included in the set of training examples. Computing device, processor, and/or module may automatically generate a missing training example; this may be done by receiving and/or retrieving a missing input and/or output value and correlating the missing input and/or output value with a corresponding output and/or input value collocated in a data record with the retrieved value, provided by a user and/or other device, or the like.

Continuing to refer to FIG. 4, computer, processor, and/or module may be configured to preprocess training data. "Preprocessing" training data, as used in this disclosure, is transforming training data from raw form to a format that can be used for training a machine learning model. Preprocessing may include sanitizing, feature selection, feature scaling, data augmentation and the like.

Still referring to FIG. 4, computer, processor, and/or module may be configured to sanitize training data. "Sanitizing" training data, as used in this disclosure, is a process whereby training examples are removed that interfere with convergence of a machine-learning model and/or process to a useful result. For instance, and without limitation, a training example may include an input and/or output value that is an outlier from typically encountered values, such that a machine-learning algorithm using the training example will be adapted to an unlikely amount as an input and/or output; a value that is more than a threshold number of standard deviations away from an average, mean, or expected value, for instance, may be eliminated. Alternatively or additionally, one or more training examples may be identified as having poor quality data, where "poor quality" is defined as having a signal to noise ratio below a threshold value. Sanitizing may include steps such as removing duplicative or otherwise redundant data, interpolating missing data, correcting data errors, standardizing data, identifying outliers, and the like. In a nonlimiting example, sanitization may include utilizing algorithms for identifying duplicate entries or spell-check algorithms.

As a non-limiting example, and with further reference to FIG. 4, images used to train an image classifier or other machine-learning model and/or process that takes images as inputs or generates images as outputs may be rejected if image quality is below a threshold value. For instance, and without limitation, computing device, processor, and/or module may perform blur detection, and eliminate one or more Blur detection may be performed, as a non-limiting example, by taking Fourier transform, or an approximation such as a Fast Fourier Transform (FFT) of the image and analyzing a distribution of low and high frequencies in the resulting frequency-domain depiction of the image; numbers of high-frequency values below a threshold level may indicate blurriness. As a further non-limiting example, detection of blurriness may be performed by convolving an image, a channel of an image, or the like with a Laplacian kernel; this may generate a numerical score reflecting a number of rapid changes in intensity shown in the image, such that a high score indicates clarity and a low score indicates blurriness. Blurriness detection may be performed using a gradient-based operator, which measures operators based on the gradient or first derivative of an image, based on the hypothesis that rapid changes indicate sharp edges in the image, and thus are indicative of a lower degree of blurriness. Blur detection may be performed using Wavelet-based operator, which takes advantage of the capability of coefficients of the discrete wavelet transform to describe the frequency and spatial content of images. Blur detection may be performed using statistics-based operators take advantage of several image statistics as texture descriptors in order to compute a focus level. Blur detection may be performed by using discrete cosine transform (DCT) coefficients in order to compute a focus level of an image from its frequency content.

Continuing to refer to FIG. 4, computing device, processor, and/or module may be configured to precondition one or more training examples. For instance, and without limitation, where a machine learning model and/or process has one or more inputs and/or outputs requiring, transmitting, or receiving a certain number of bits, samples, or other units of data, one or more training examples' elements to be used as or compared to inputs and/or outputs may be modified to have such a number of units of data. For instance, a computing device, processor, and/or module may convert a smaller number of units, such as in a low pixel count image, into a desired number of units, for instance by upsampling and interpolating. As a non-limiting example, a low pixel count image may have 100 pixels, however a desired number of pixels may be 128. Processor may interpolate the low pixel count image to convert the 100 pixels into 128 pixels. It should also be noted that one of ordinary skill in the art, upon reading this disclosure, would know the various methods to interpolate a smaller number of data units such as samples, pixels, bits, or the like to a desired number of such units. In some instances, a set of interpolation rules may be trained by sets of highly detailed inputs and/or outputs and corresponding inputs and/or outputs downsampled to smaller numbers of units, and a neural network or other machine learning model that is trained to predict interpolated pixel values using the training data. As a non-limiting example, a sample input and/or output, such as a sample picture, with sample-expanded data units (e.g., pixels added between the original pixels) may be input to a neural network or machine-learning model and output a pseudo replica sample-picture with dummy values assigned to pixels between the original pixels based on a set of interpolation rules. As a non-limiting example, in the context of an image classifier, a machine-learning model may have a set of interpolation rules trained by sets of highly detailed images and images that have been downsampled to smaller numbers of pixels, and a neural network or other machine learning model that is trained using those examples to predict interpolated pixel values in a facial picture context. As a result, an input with sample-expanded data units (the ones added between the original data units, with dummy values) may be run through a trained neural network and/or model, which may fill in values to replace the dummy values. Alternatively or additionally, processor, computing device, and/or module may utilize sample expander methods, a low-pass filter, or both. As used in this disclosure, a "low-pass filter" is a filter that passes signals with a frequency lower than a selected cutoff frequency and attenuates signals with frequencies higher than the cutoff frequency. The exact frequency response of the filter depends on the filter design. Computing device, processor, and/or module may use averaging, such as luma or chroma averaging in images, to fill in data units in between original data units.

In some embodiments, and with continued reference to FIG. 4, computing device, processor, and/or module may down-sample elements of a training example to a desired lower number of data elements. As a non-limiting example, a high pixel count image may have 256 pixels, however a desired number of pixels may be 128. Processor may downsample the high pixel count image to convert the 256 pixels into 128 pixels. In some embodiments, processor may be configured to perform downsampling on data. Downsampling, also known as decimation, may include removing every Nth entry in a sequence of samples, all but every Nth entry, or the like, which is a process known as "compression," and may be performed, for instance by an N-sample compressor implemented using hardware or software. Anti-aliasing and/or anti-imaging filters, and/or low-pass filters, may be used to clean up side-effects of compression.

Further referring to FIG. 4, feature selection includes narrowing and/or filtering training data to exclude features and/or elements, or training data including such elements, that are not relevant to a purpose for which a trained machine-learning model and/or algorithm is being trained, and/or collection of features and/or elements, or training data including such elements, on the basis of relevance or utility for an intended task or purpose for a trained machine-learning model and/or algorithm is being trained. Feature selection may be implemented, without limitation, using any process described in this disclosure, including without limitation using training data classifiers, exclusion of outliers, or the like.

With continued reference to FIG. 4, feature scaling may include, without limitation, normalization of data entries, which may be accomplished by dividing numerical fields by norms thereof, for instance as performed for vector normalization. Feature scaling may include absolute maximum scaling, wherein each quantitative datum is divided by the maximum absolute value of all quantitative data of a set or subset of quantitative data. Feature scaling may include min-max scaling, in which each value X has a minimum value $X_{min}$ in a set or subset of values subtracted therefrom, with the result divided by the range of the values, give maximum value in the set or subset $$X_{max}: X_{new} = \frac{X - X_{min}}{X_{max} - X_{min}}.$$

Feature scaling may include mean normalization, which involves use of a mean value of a set and/or subset of values, $X_{mean}$ with maximum and minimum values:

$$X_{new} = \frac{X - X_{mean}}{X_{max} - X_{min}}.$$

Feature scaling may include standardization, where a difference between X and $X_{mean}$ is divided by a standard deviation $\sigma$ of a set or subset of values:

$$X_{new} = \frac{X - X_{mean}}{\sigma}.$$

Scaling may be performed using a median value of a a set or subset $X_{median}$ and/or interquartile range (IQR), which represents the difference between the $25^{th}$ percentile value and the $50^{th}$ percentile value (or closest values thereto by a rounding protocol), such as:

$$X_{new} = \frac{X - X_{median}}{IQR}.$$

Persons skilled in the art, upon reviewing the entirety of this disclosure, will be aware of various alternative or additional approaches that may be used for feature scaling.

Further referring to FIG. 4, computing device, processor, and/or module may be configured to perform one or more processes of data augmentation. "Data augmentation" as used in this disclosure is addition of data to a training set using elements and/or entries already in the dataset. Data augmentation may be accomplished, without limitation, using interpolation, generation of modified copies of existing entries and/or examples, and/or one or more generative AI processes, for instance using deep neural networks and/or generative adversarial networks; generative processes may be referred to alternatively in this context as "data synthesis" and as creating "synthetic data." Augmentation may include performing one or more transformations on data, such as geometric, color space, affine, brightness, cropping, and/or contrast transformations of images.

Still referring to FIG. 4, machine-learning module 400 may be configured to perform a lazy-learning process 420 and/or protocol, which may alternatively be referred to as a "lazy loading" or "call-when-needed" process and/or protocol, may be a process whereby machine learning is conducted upon receipt of an input to be converted to an output, by combining the input and training set to derive the algorithm to be used to produce the output on demand. For instance, an initial set of simulations may be performed to cover an initial heuristic and/or "first guess" at an output and/or relationship. As a non-limiting example, an initial heuristic may include a ranking of associations between inputs and elements of training data 404. Heuristic may include selecting some number of highest-ranking associations and/or training data 404 elements. Lazy learning may implement any suitable lazy learning algorithm, including without limitation a K-nearest neighbors algorithm, a lazy naïve Bayes algorithm, or the like; persons skilled in the art, upon reviewing the entirety of this disclosure, will be aware of various lazy-learning algorithms that may be applied to generate outputs as described in this disclosure, including without limitation lazy learning applications of machine-learning algorithms as described in further detail below.

Alternatively or additionally, and with continued reference to FIG. 4, machine-learning processes as described in this disclosure may be used to generate machine-learning models 424. A "machine-learning model," as used in this disclosure, is a data structure representing and/or instantiating a mathematical and/or algorithmic representation of a relationship between inputs and outputs, as generated using any machine-learning process including without limitation any process as described above, and stored in memory; an input is submitted to a machine-learning model 424 once created, which generates an output based on the relationship that was derived. For instance, and without limitation, a linear regression model, generated using a linear regression algorithm, may compute a linear combination of input data using coefficients derived during machine-learning processes to calculate an output datum. As a further non-limiting example, a machine-learning model 424 may be generated by creating an artificial neural network, such as a convolutional neural network comprising an input layer of nodes, one or more intermediate layers, and an output layer of nodes. Connections between nodes may be created via the process of "training" the network, in which elements from a training data 404 set are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning.

Still referring to FIG. 4, machine-learning algorithms may include at least a supervised machine-learning process 428. At least a supervised machine-learning process 428, as defined herein, include algorithms that receive a training set relating a number of inputs to a number of outputs, and seek to generate one or more data structures representing and/or instantiating one or more mathematical relations relating inputs to outputs, where each of the one or more mathematical relations is optimal according to some criterion specified to the algorithm using some scoring function. For instance, a supervised learning algorithm may include inputs as described above as inputs and outputs as described above as outputs, and a scoring function representing a desired form of relationship to be detected between inputs and outputs; scoring function may, for instance, seek to maximize the probability that a given input and/or combination of elements inputs is associated with a given output to minimize the probability that a given input is not associated with a given output. Scoring function may be expressed as a risk function representing an "expected loss" of an algorithm relating inputs to outputs, where loss is computed as an error function representing a degree to which a prediction generated by the relation is incorrect when compared to a given input-output pair provided in training data 404. Persons skilled in the art, upon reviewing the entirety of this disclosure, will be aware of various possible variations of at least a supervised machine-learning process 428 that may be used to determine relation between inputs and outputs. Supervised machine-learning processes may include classification algorithms as defined above.

With further reference to FIG. 4, training a supervised machine-learning process may include, without limitation, iteratively updating coefficients, biases, weights based on an error function, expected loss, and/or risk function. For instance, an output generated by a supervised machine-learning model using an input example in a training example may be compared to an output example from the training example; an error function may be generated based on the comparison, which may include any error function suitable for use with any machine-learning algorithm described in this disclosure, including a square of a difference between one or more sets of compared values or the like. Such an error function may be used in turn to update one or more weights, biases, coefficients, or other parameters of a machine-learning model through any suitable process including without limitation gradient descent processes, least-squares processes, and/or other processes described in this disclosure. This may be done iteratively and/or recursively to gradually tune such weights, biases, coefficients, or other parameters. Updating may be performed, in neural networks, using one or more back-propagation algorithms. Iterative and/or recursive updates to weights, biases, coefficients, or other parameters as described above may be performed until currently available training data is exhausted and/or until a convergence test is passed, where a "convergence test" is a test for a condition selected as indicating that a model and/or weights, biases, coefficients, or other parameters thereof has reached a degree of accuracy. A convergence test may, for instance, compare a difference between two or more successive errors or error function values, where differences below a threshold amount may be taken to indicate convergence. Alternatively or additionally, one or more errors and/or error function values evaluated in training iterations may be compared to a threshold.

Still referring to FIG. 4, a computing device, processor, and/or module may be configured to perform method, method step, sequence of method steps and/or algorithm described in reference to this figure, in any order and with any degree of repetition. For instance, a computing device, processor, and/or module may be configured to perform a single step, sequence and/or algorithm repeatedly until a desired or commanded outcome is achieved; repetition of a step or a sequence of steps may be performed iteratively and/or recursively using outputs of previous repetitions as inputs to subsequent repetitions, aggregating inputs and/or outputs of repetitions to produce an aggregate result, reduction or decrement of one or more variables such as global variables, and/or division of a larger processing task into a set of iteratively addressed smaller processing tasks. A computing device, processor, and/or module may perform any step, sequence of steps, or algorithm in parallel, such as simultaneously and/or substantially simultaneously performing a step two or more times using two or more parallel threads, processor cores, or the like; division of tasks between parallel threads and/or processes may be performed according to any protocol suitable for division of tasks between iterations. Persons skilled in the art, upon reviewing the entirety of this disclosure, will be aware of various ways in which steps, sequences of steps, processing tasks, and/or data may be subdivided, shared, or otherwise dealt with using iteration, recursion, and/or parallel processing.

Further referring to FIG. 4, machine learning processes may include at least an unsupervised machine-learning processes 432. An unsupervised machine-learning process, as used herein, is a process that derives inferences in datasets without regard to labels; as a result, an unsupervised machine-learning process may be free to discover any structure, relationship, and/or correlation provided in the data. Unsupervised processes 432 may not require a response variable; unsupervised processes 432 may be used to find interesting patterns and/or inferences between variables, to determine a degree of correlation between two or more variables, or the like.

Still referring to FIG. 4, machine-learning module 400 may be designed and configured to create a machine-learning model 424 using techniques for development of linear regression models. Linear regression models may include ordinary least squares regression, which aims to minimize the square of the difference between predicted outcomes and actual outcomes according to an appropriate norm for measuring such a difference (e.g. a vector-space distance norm); coefficients of the resulting linear equation may be modified to improve minimization. Linear regression models may include ridge regression methods, where the function to be minimized includes the least-squares function plus term multiplying the square of each coefficient by a scalar amount to penalize large coefficients. Linear regression models may include least absolute shrinkage and selection operator (LASSO) models, in which ridge regression is combined with multiplying the least-squares term by a factor of 1 divided by double the number of samples. Linear regression models may include a multi-task lasso model wherein the norm applied in the least-squares term of the lasso model is the Frobenius norm amounting to the square root of the sum of squares of all terms. Linear regression models may include the elastic net model, a multi-task elastic net model, a least angle regression model, a LARS lasso model, an orthogonal matching pursuit model, a Bayesian regression model, a logistic regression model, a stochastic gradient descent model, a perceptron model, a passive aggressive algorithm, a robustness regression model, a Huber regression model, or any other suitable model that may occur to persons skilled in the art upon reviewing the entirety of this disclosure. Linear regression models may be generalized in an embodiment to polynomial regression models, whereby a polynomial equation (e.g. a quadratic, cubic or higher-order equation) providing a best predicted output/actual output fit is sought; similar methods to those described above may be applied to minimize error functions, as will be apparent to persons skilled in the art upon reviewing the entirety of this disclosure.

Continuing to refer to FIG. 4, machine-learning algorithms may include, without limitation, linear discriminant analysis. Machine-learning algorithm may include quadratic discriminant analysis. Machine-learning algorithms may include kernel ridge regression. Machine-learning algorithms may include support vector machines, including without limitation support vector classification-based regression processes. Machine-learning algorithms may include stochastic gradient descent algorithms, including classification and regression algorithms based on stochastic gradient descent. Machine-learning algorithms may include nearest neighbors algorithms. Machine-learning algorithms may include various forms of latent space regularization such as variational regularization. Machine-learning algorithms may include Gaussian processes such as Gaussian Process Regression. Machine-learning algorithms may include cross-decomposition algorithms, including partial least squares and/or canonical correlation analysis. Machine-learning algorithms may include naïve Bayes methods. Machine-learning algorithms may include algorithms based on decision trees, such as decision tree classification or regression algorithms. Machine-learning algorithms may include ensemble methods such as bagging meta-estimator, forest of randomized trees, AdaBoost, gradient tree boosting, and/or voting classifier methods. Machine-learning algorithms may include neural net algorithms, including convolutional neural net processes.

Still referring to FIG. 4, a machine-learning model and/or process may be deployed or instantiated by incorporation into a program, apparatus, system and/or module. For instance, and without limitation, a machine-learning model, neural network, and/or some or all parameters thereof may be stored and/or deployed in any memory or circuitry. Parameters such as coefficients, weights, and/or biases may be stored as circuit-based constants, such as arrays of wires and/or binary inputs and/or outputs set at logic "1" and "0" voltage levels in a logic circuit to represent a number according to any suitable encoding system including twos complement or the like or may be stored in any volatile and/or non-volatile memory. Similarly, mathematical operations and input and/or output of data to or from models, neural network layers, or the like may be instantiated in hardware circuitry and/or in the form of instructions in firmware, machine-code such as binary operation code instructions, assembly language, or any higher-order programming language. Any technology for hardware and/or software instantiation of memory, instructions, data structures, and/or algorithms may be used to instantiate a machine-learning process and/or model, including without limitation any combination of production and/or configuration of non-reconfigurable hardware elements, circuits, and/or modules such as without limitation ASICs, production and/or configuration of reconfigurable hardware elements, circuits, and/or modules such as without limitation FPGAs, production and/or of non-reconfigurable and/or configuration non-rewritable memory elements, circuits, and/or modules such as without limitation non-rewritable ROM, production and/or configuration of reconfigurable and/or rewritable memory elements, circuits, and/or modules such as without limitation rewritable ROM or other memory technology described in this disclosure, and/or production and/or configuration of any computing device and/or component thereof as described in this disclosure. Such deployed and/or instantiated machine-learning model and/or algorithm may receive inputs from any other process, module, and/or component described in this disclosure, and produce outputs to any other process, module, and/or component described in this disclosure.

Continuing to refer to FIG. 4, any process of training, retraining, deployment, and/or instantiation of any machine-learning model and/or algorithm may be performed and/or repeated after an initial deployment and/or instantiation to correct, refine, and/or improve the machine-learning model and/or algorithm. Such retraining, deployment, and/or instantiation may be performed as a periodic or regular process, such as retraining, deployment, and/or instantiation at regular elapsed time periods, after some measure of volume such as a number of bytes or other measures of data processed, a number of uses or performances of processes described in this disclosure, or the like, and/or according to a software, firmware, or other update schedule. Alternatively or additionally, retraining, deployment, and/or instantiation may be event-based, and may be triggered, without limitation, by user inputs indicating sub-optimal or otherwise problematic performance and/or by automated field testing and/or auditing processes, which may compare outputs of machine-learning models and/or algorithms, and/or errors and/or error functions thereof, to any thresholds, convergence tests, or the like, and/or may compare outputs of processes described herein to similar thresholds, convergence tests or the like. Event-based retraining, deployment, and/or instantiation may alternatively or additionally be triggered by receipt and/or generation of one or more new training examples; a number of new training examples may be compared to a preconfigured threshold, where exceeding the preconfigured threshold may trigger retraining, deployment, and/or instantiation.

Still referring to FIG. 4, retraining and/or additional training may be performed using any process for training described above, using any currently or previously deployed version of a machine-learning model and/or algorithm as a starting point. Training data for retraining may be collected, preconditioned, sorted, classified, sanitized or otherwise processed according to any process described in this disclosure. Training data may include, without limitation, training examples including inputs and correlated outputs used, received, and/or generated from any version of any system, module, machine-learning model or algorithm, apparatus, and/or method described in this disclosure; such examples may be modified and/or labeled according to user feedback or other processes to indicate desired results, and/or may have actual or measured results from a process being modeled and/or predicted by system, module, machine-learning model or algorithm, apparatus, and/or method as "desired" results to be compared to outputs for training processes as described above.

Redeployment may be performed using any reconfiguring and/or rewriting of reconfigurable and/or rewritable circuit and/or memory elements; alternatively, redeployment may be performed by production of new hardware and/or software components, circuits, instructions, or the like, which may be added to and/or may replace existing hardware and/or software components, circuits, instructions, or the like.

Further referring to FIG. 4, one or more processes or algorithms described above may be performed by at least a dedicated hardware unit 436. A "dedicated hardware unit," for the purposes of this figure, is a hardware component, circuit, or the like, aside from a principal control circuit and/or processor performing method steps as described in this disclosure, that is specifically designated or selected to perform one or more specific tasks and/or processes described in reference to this figure, such as without limitation preconditioning and/or sanitization of training data and/or training a machine-learning algorithm and/or model. A dedicated hardware unit 436 may include, without limitation, a hardware unit that can perform iterative or massed calculations, such as matrix-based calculations to update or tune parameters, weights, coefficients, and/or biases of machine-learning models and/or neural networks, efficiently using pipelining, parallel processing, or the like; such a hardware unit may be optimized for such processes by, for instance, including dedicated circuitry for matrix and/or signal processing operations that includes, e.g., multiple arithmetic and/or logical circuit units such as multipliers and/or adders that can act simultaneously and/or in parallel or the like. Such dedicated hardware units 436 may include, without limitation, graphical processing units (GPUs), dedicated signal processing modules, FPGA or other reconfigurable hardware that has been configured to instantiate parallel processing units for one or more specific tasks, or the like, A computing device, processor, apparatus, or module may be configured to instruct one or more dedicated hardware units 436 to perform one or more operations described herein, such as evaluation of model and/or algorithm outputs, one-time or iterative updates to parameters, coefficients, weights, and/or biases, and/or any other operations such as vector and/or matrix operations as described in this disclosure.

Figure 5:
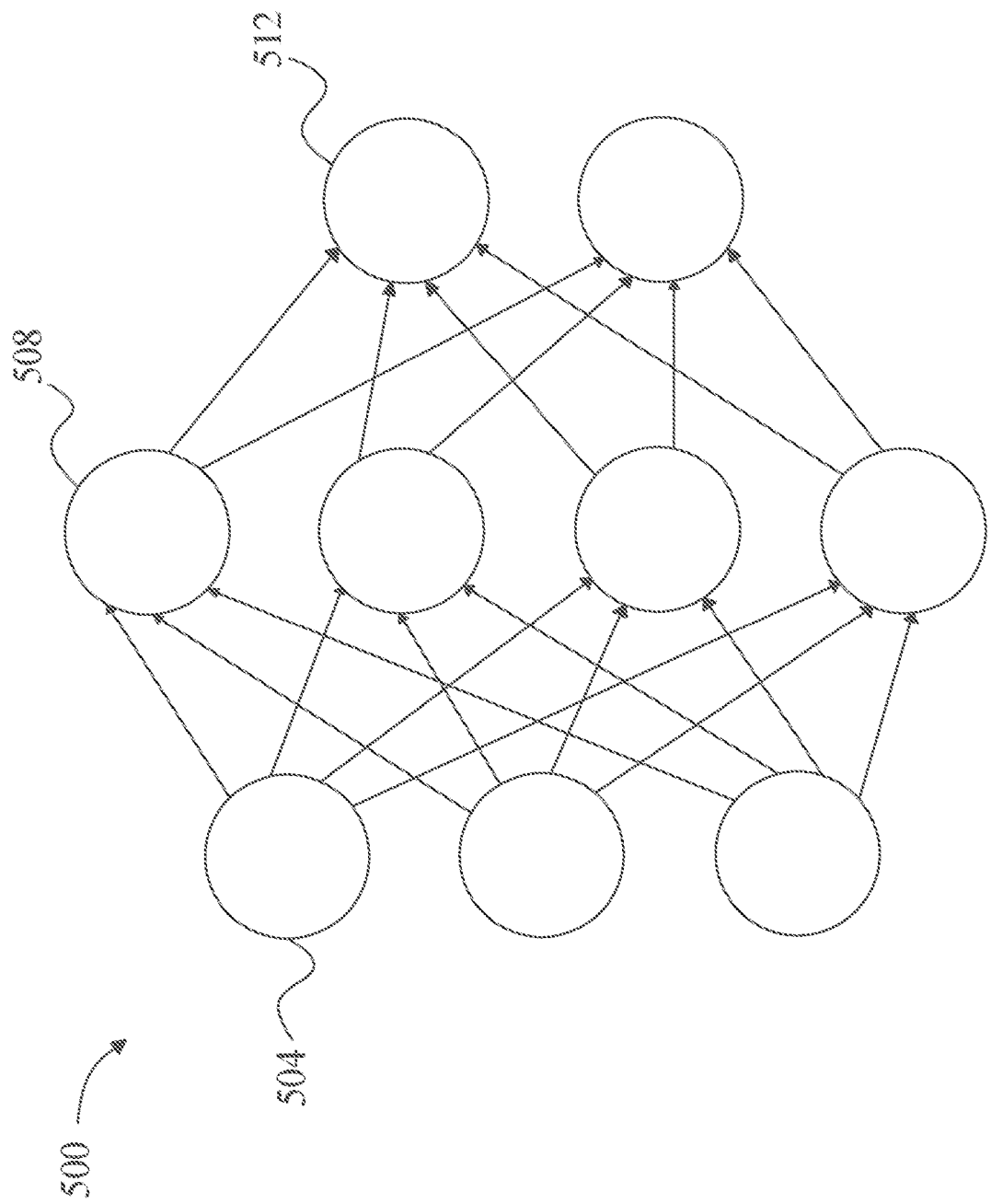
FIG. 5 is a diagram of an exemplary embodiment of a neural network.

Referring now to FIG. 5, an exemplary embodiment of neural network 500 is illustrated. A neural network 500 also known as an artificial neural network, is a network of "nodes," or data structures having one or more inputs, one or more outputs, and a function determining outputs based on inputs. Such nodes may be organized in a network, such as without limitation a convolutional neural network, including an input layer of nodes 504, one or more intermediate layers 508, and an output layer of nodes 512. Connections between nodes may be created via the process of "training" the network, in which elements from a training dataset are applied to the input nodes, a suitable training algorithm (such as Levenberg-Marquardt, conjugate gradient, simulated annealing, or other algorithms) is then used to adjust the connections and weights between nodes in adjacent layers of the neural network to produce the desired values at the output nodes. This process is sometimes referred to as deep learning. Connections may run solely from input nodes toward output nodes in a "feed-forward" network, or may feed outputs of one layer back to inputs of the same or a different layer in a "recurrent network." As a further non-limiting example, a neural network may include a convolutional neural network comprising an input layer of nodes, one or more intermediate layers, and an output layer of nodes. A "convolutional neural network," as used in this disclosure, is a neural network in which at least one hidden layer is a convolutional layer that convolves inputs to that layer with a subset of inputs known as a "kernel," along with one or more additional layers such as pooling layers, fully connected layers, and the like.

Figure 6:
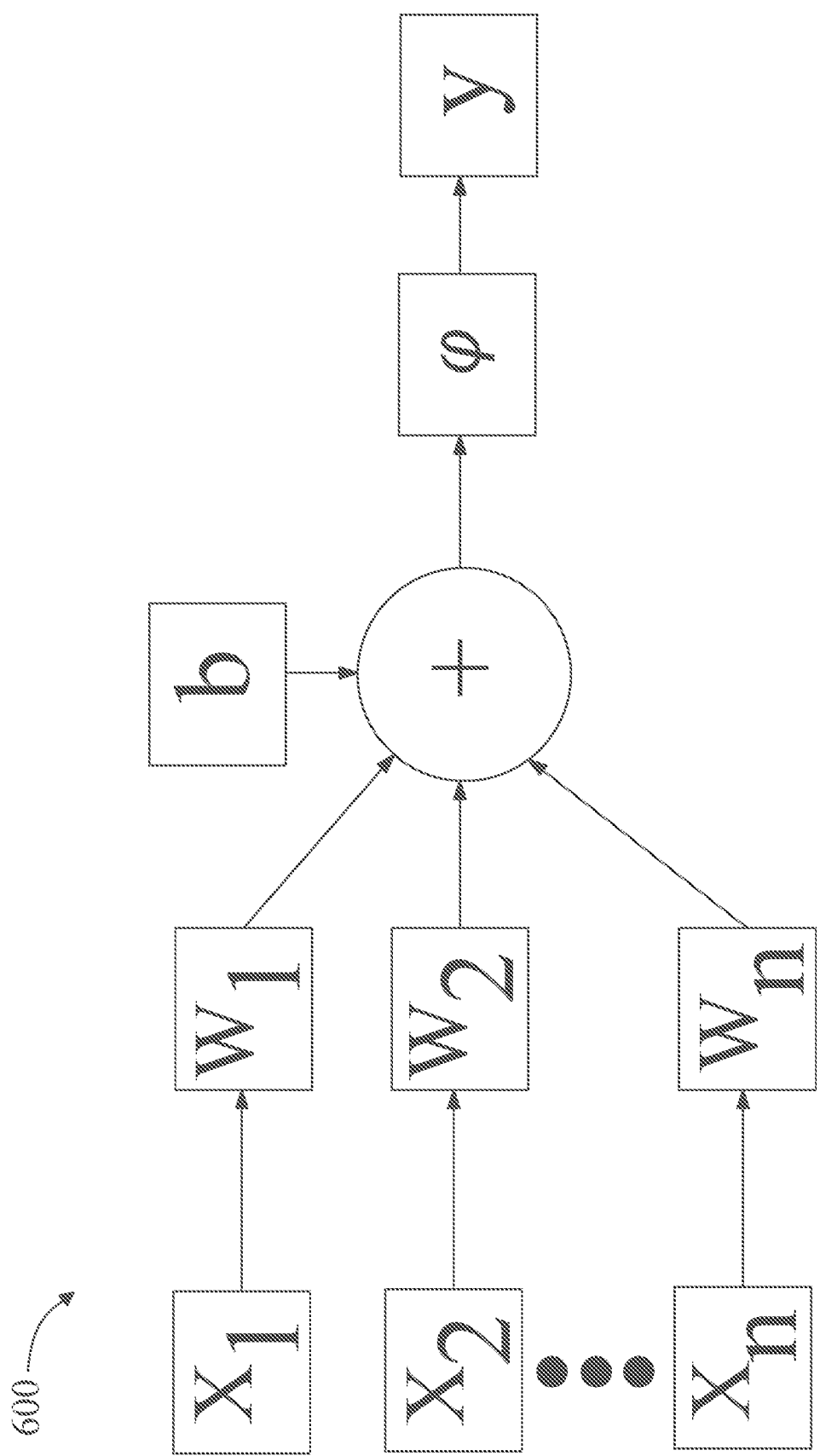
FIG. 6 is a diagram of an exemplary embodiment of a node of a neural network.

Referring now to FIG. 6, an exemplary embodiment of a node 600 of a neural network is illustrated. A node may include, without limitation a plurality of inputs $x_i$ that may receive numerical values from inputs to a neural network containing the node and/or from other nodes. Node may perform one or more activation functions to produce its output given one or more inputs, such as without limitation computing a binary step function comparing an input to a threshold value and outputting either a logic 1 or logic 0 output or something equivalent, a linear activation function whereby an output is directly proportional to the input, and/or a non-linear activation function, wherein the output is not proportional to the input. Non-linear activation functions may include, without limitation, a sigmoid function of the form $$f(x) = \frac{1}{1-e^{-x}}$$

given input x, a tan h (hyperbolic tangent) function, of the form $$\frac{e^x - e^{-x}}{e^x + e^{-x}},$$

a tan h derivative function such as ƒ(x)=tan h² (x), a rectified linear unit function such as ƒ(x)=max (0, x), a "leaky" and/or "parametric" rectified linear unit function such as ƒ(x)=max (ax, x) for some a, an exponential linear units function such as $$f(x) = \begin{cases} x & \text{for } x \geq 0 \\ \alpha(e^x - 1) & \text{for } x < 0 \end{cases}$$

for some value of α (this function may be replaced and/or weighted by its own derivative in some embodiments), a softmax function such as $$f(x_i) = \frac{e^x}{\sum_i x_i}$$

where the inputs to an instant layer are $x_i$, a swish function such as ƒ(x)=x*sigmoid (x), a Gaussian error linear unit function such as f(x)=a(1+tan h($\sqrt{2/\pi}$(x+bx^r))) for some values of a, b, and r, and/or a scaled exponential linear unit function such as $$f(x) = \lambda \begin{cases} \alpha(e^x - 1) & \text{for } x < 0 \\ x & \text{for } x \geq 0 \end{cases}.$$

Fundamentally, there is no limit to the nature of functions of inputs $x_i$ that may be used as activation functions. As a non-limiting and illustrative example, node may perform a weighted sum of inputs using weights $w_i$ that are multiplied by respective inputs $x_i$. Additionally or alternatively, a bias b may be added to the weighted sum of the inputs such that an offset is added to each unit in the neural network layer that is independent of the input to the layer. The weighted sum may then be input into a function φ, which may generate one or more outputs y. Weight $w_i$ applied to an input $x_i$ may indicate whether the input is "excitatory," indicating that it has strong influence on the one or more outputs y, for instance by the corresponding weight having a large numerical value, and/or a "inhibitory," indicating it has a weak effect influence on the one more inputs y, for instance by the corresponding weight having a small numerical value. The values of weights $w_i$ may be determined by training a neural network using training data, which may be performed using any suitable process as described above.

Figure 7:
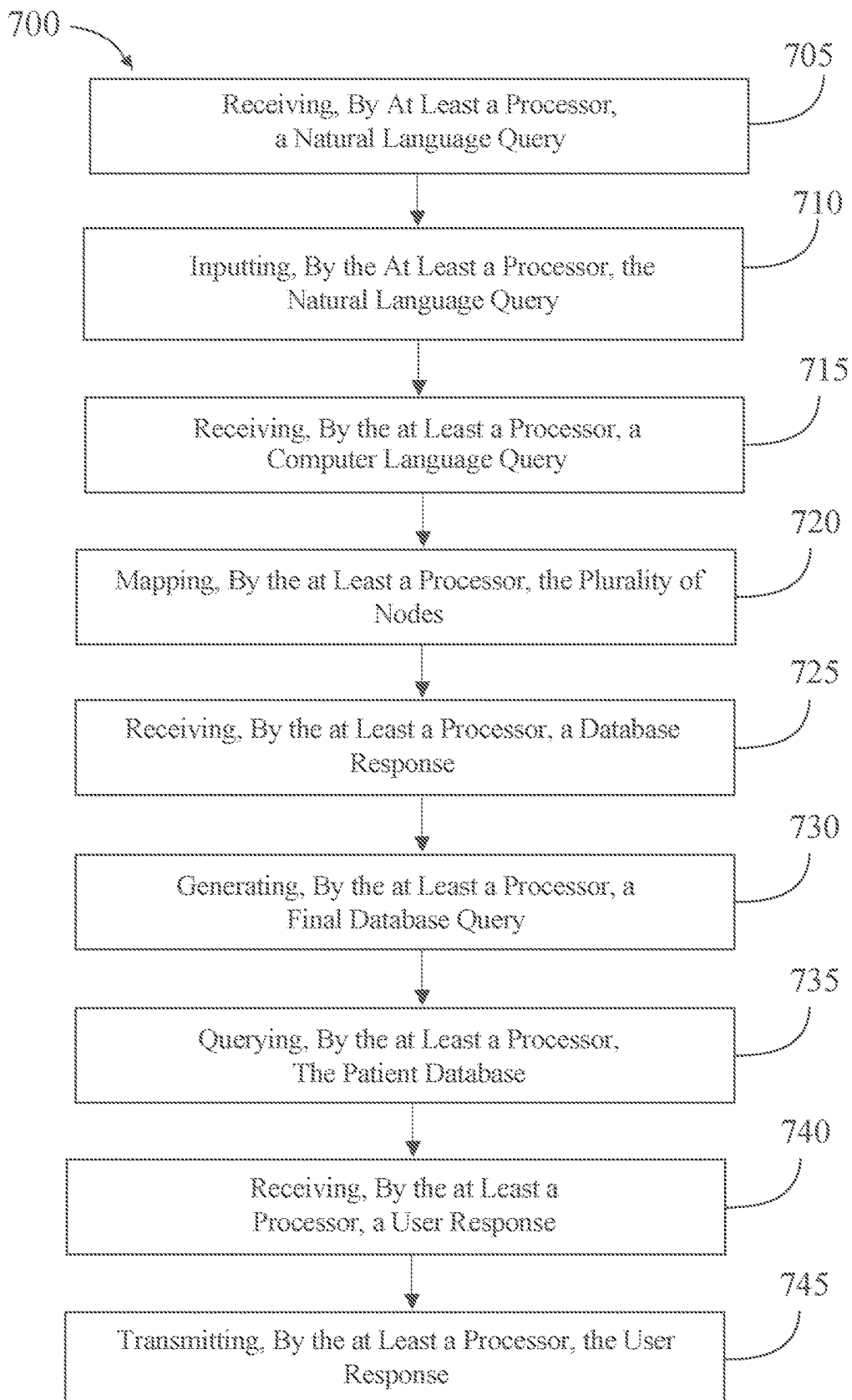
FIG. 7 is a flow diagram illustrating an exemplary embodiment of a method retrieving patient information using large language models in accordance with the subject disclosure.

Referring now to FIG. 7, a method 700 for retrieving patient information using large language models is described. At step 705, method 700 includes receiving, by at least a processor, a natural language query as a function of a user input. In one or more embodiments, receiving, by the at least a processor, the natural language query as a function of the user input includes receiving the natural language query using a chatbot method. This may be implemented with reference to FIGS. 1-7 and without limitation.

With continued reference to FIG. 7, at step 710 method 700 includes inputting, by the least a processor, the natural language query into a large language model communicatively connected to the least a processor. This may be implemented with reference to FIGS. 1-7 and without limitation.

With continued reference to FIG. 7, at step 715 method 700 includes receiving, by the at least a processor, a computer language query including a plurality of nodes from the large language model. In one or more embodiments, receiving, by the at least a processor, the computer language query including the plurality of nodes from the large language model includes identifying one or more atomic elements as a function of the natural language query; and generating the computer language query as a function of the identification. This may be implemented with reference to FIGS. 1-7 and without limitation.

With continued reference to FIG. 7, at step 720 method 700 includes mapping, by the at least a processor, the plurality of nodes to one or more entries in a patient database. This may be implemented with reference to FIGS. 1-7 and without limitation.

With continued reference to FIG. 7, at step 725 method 700 includes receiving, by the at least a processor, a database response from the patient database as a function of the mapping. In one or more embodiments, receiving, by the at least a processor, the database response from the patient database includes extracting one or more patient cohorts as a function of the one or more atomic elements. This may be implemented with reference to FIGS. 1-7 and without limitation.

With continued reference to FIG. 7, at step 730, method 700 includes generating, by the at least a processor, a final database query as a function of the database response. In one or more embodiments, generating, by the at least a processor, the final database query as a function of the database response includes generating a plurality of logical relationships between the plurality of nodes as a function of the database response and generating the final database query as a function of the logical relationships and the database response. In one or more embodiments, wherein generating the plurality of logical relationships includes determining a temporal relationship between atomic elements within the natural language query. This may be implemented with reference to FIGS. 1-7 and without limitation.

With continued reference to FIG. 7, at step 735 method 700 includes querying, by the at least a processor, the patient database using the final database query. This may be implemented with reference to FIGS. 1-7 and without limitation.

With continued reference to FIG. 7, at step 740 method 700 includes receiving by the at least a processor, a user response as a function of the final database query. This may be implemented with reference to FIGS. 1-7 and without limitation.

With continued reference to FIG. 7, at step 745 method 700 includes transmitting, by the at least a processor, the user response to a graphical user interface as a function of the final database query. In one or more embodiments, transmitting, by the at least a processor, the user response to the graphical user interface as a function of the final database query includes generating a user interface data structure comprising at least the user response and transmitting the user response to the graphical user interface as a function of the user interface data structure. In one or more embodiments, transmitting, by the at least a processor, the user response to the graphical user interface as a function of the final database query includes transmitting the user response to the large language model, generating a natural language response using the large language model as a function of the user response and transmitting the natural language response to the graphical user interface. In one or more embodiments, generating, by the at least a processor, the natural language response using the large language model as a function of the user response includes generating the natural language response as a function of a user profile. In one or more embodiments, generating the natural language response as a function of the user profile includes classifying the user profile to one or more language groupings. This may be implemented with reference to FIGS. 1-7 and without limitation.

It is to be noted that any one or more of the aspects and embodiments described herein may be conveniently implemented using one or more machines (e.g., one or more computing devices that are utilized as a user computing device for an electronic document, one or more server devices, such as a document server, etc.) programmed according to the teachings of the present specification, as will be apparent to those of ordinary skill in the computer art. Appropriate software coding can readily be prepared by skilled programmers based on the teachings of the present disclosure, as will be apparent to those of ordinary skill in the software art. Aspects and implementations discussed above employing software and/or software modules may also include appropriate hardware for assisting in the implementation of the machine executable instructions of the software and/or software module.

Such software may be a computer program product that employs a machine-readable storage medium. A machine-readable storage medium may be any medium that is capable of storing and/or encoding a sequence of instructions for execution by a machine (e.g., a computing device) and that causes the machine to perform any one of the methodologies and/or embodiments described herein. Examples of a machine-readable storage medium include, but are not limited to, a magnetic disk, an optical disc (e.g., CD, CD-R, DVD, DVD-R, etc.), a magneto-optical disk, a read-only memory "ROM" device, a random access memory "RAM" device, a magnetic card, an optical card, a solid-state memory device, an EPROM, an EEPROM, and any combinations thereof. A machine-readable medium, as used herein, is intended to include a single medium as well as a collection of physically separate media, such as, for example, a collection of compact discs or one or more hard disk drives in combination with a computer memory. As used herein, a machine-readable storage medium does not include transitory forms of signal transmission.

Such software may also include information (e.g., data) carried as a data signal on a data carrier, such as a carrier wave. For example, machine-executable information may be included as a data-carrying signal embodied in a data carrier in which the signal encodes a sequence of instruction, or portion thereof, for execution by a machine (e.g., a computing device) and any related information (e.g., data structures and data) that causes the machine to perform any one of the methodologies and/or embodiments described herein.

Examples of a computing device include, but are not limited to, an electronic book reading device, a computer workstation, a terminal computer, a server computer, a handheld device (e.g., a tablet computer, a smartphone, etc.), a web appliance, a network router, a network switch, a network bridge, any machine capable of executing a sequence of instructions that specify an action to be taken by that machine, and any combinations thereof. In one example, a computing device may include and/or be included in a kiosk.

Figure 8:
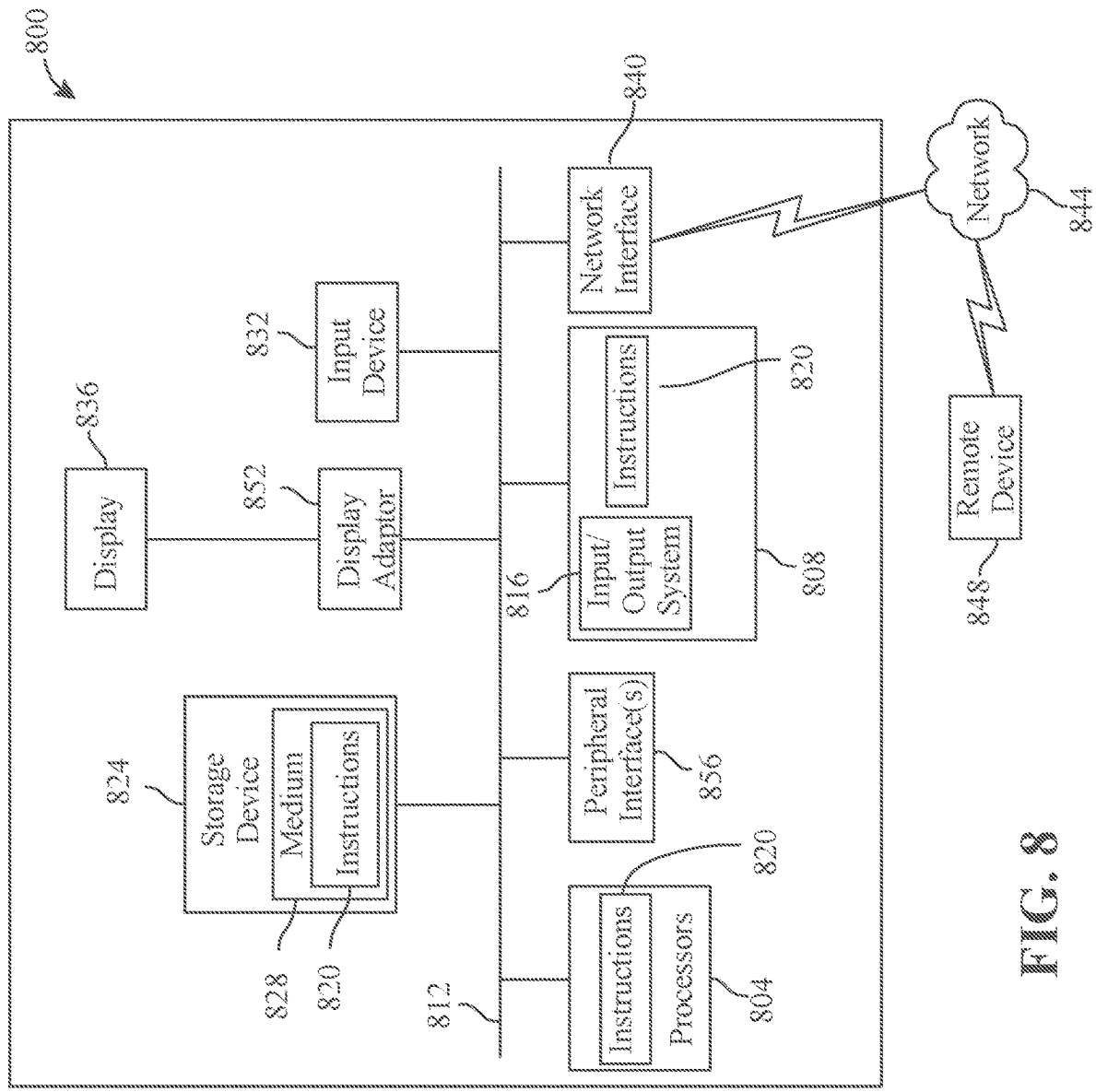
FIG. 8 is a block diagram of a computing system that can be used to implement any one or more of the methodologies disclosed herein and any one or more portions thereof.

FIG. 8 shows a diagrammatic representation of one embodiment of a computing device in the exemplary form of a computer system 800 within which a set of instructions for causing a control system to perform any one or more of the aspects and/or methodologies of the present disclosure may be executed. It is also contemplated that multiple computing devices may be utilized to implement a specially configured set of instructions for causing one or more of the devices to perform any one or more of the aspects and/or methodologies of the present disclosure. Computer system 800 includes a processor 804 and a memory 808 that communicate with each other, and with other components, via a bus 812. Bus 812 may include any of several types of bus structures including, but not limited to, a memory bus, a memory controller, a peripheral bus, a local bus, and any combinations thereof, using any of a variety of bus architectures.

Processor 804 may include any suitable processor, such as without limitation a processor incorporating logical circuitry for performing arithmetic and logical operations, such as an arithmetic and logic unit (ALU), which may be regulated with a state machine and directed by operational inputs from memory and/or sensors; processor 804 may be organized according to Von Neumann and/or Harvard architecture as a non-limiting example. Processor 804 may include, incorporate, and/or be incorporated in, without limitation, a microcontroller, microprocessor, digital signal processor (DSP), Field Programmable Gate Array (FPGA), Complex Programmable Logic Device (CPLD), Graphical Processing Unit (GPU), general purpose GPU, Tensor Processing Unit (TPU), analog or mixed signal processor, Trusted Platform Module (TPM), a floating point unit (FPU), system on module (SOM), and/or system on a chip (SoC).

Memory 808 may include various components (e.g., machine-readable media) including, but not limited to, a random-access memory component, a read only component, and any combinations thereof. In one example, a basic input/output system 816 (BIOS), including basic routines that help to transfer information between elements within computer system 800, such as during start-up, may be stored in memory 808. Memory 808 may also include (e.g., stored on one or more machine-readable media) instructions (e.g., software) 820 embodying any one or more of the aspects and/or methodologies of the present disclosure. In another example, memory 808 may further include any number of program modules including, but not limited to, an operating system, one or more application programs, other program modules, program data, and any combinations thereof.

Computer system 800 may also include a storage device 824. Examples of a storage device (e.g., storage device 824) include, but are not limited to, a hard disk drive, a magnetic disk drive, an optical disc drive in combination with an optical medium, a solid-state memory device, and any combinations thereof. Storage device 824 may be connected to bus 812 by an appropriate interface (not shown). Example interfaces include, but are not limited to, SCSI, advanced technology attachment (ATA), serial ATA, universal serial bus (USB), IEEE 1394 (FIREWIRE), and any combinations thereof. In one example, storage device 824 (or one or more components thereof) may be removably interfaced with computer system 800 (e.g., via an external port connector (not shown)). Particularly, storage device 824 and an associated machine-readable medium 828 may provide nonvolatile and/or volatile storage of machine-readable instructions, data structures, program modules, and/or other data for computer system 800. In one example, software 820 may reside, completely or partially, within machine-readable medium 828. In another example, software 820 may reside, completely or partially, within processor 804.

Computer system 800 may also include an input device 832. In one example, a user of computer system 800 may enter commands and/or other information into computer system 800 via input device 832. Examples of an input device 832 include, but are not limited to, an alpha-numeric input device (e.g., a keyboard), a pointing device, a joystick, a gamepad, an audio input device (e.g., a microphone, a voice response system, etc.), a cursor control device (e.g., a mouse), a touchpad, an optical scanner, a video capture device (e.g., a still camera, a video camera), a touchscreen, and any combinations thereof. Input device 832 may be interfaced to bus 812 via any of a variety of interfaces (not shown) including, but not limited to, a serial interface, a parallel interface, a game port, a USB interface, a FIRE-WIRE interface, a direct interface to bus 812, and any combinations thereof. Input device 832 may include a touch screen interface that may be a part of or separate from display 836, discussed further below. Input device 832 may be utilized as a user selection device for selecting one or more graphical representations in a graphical interface as described above.

A user may also input commands and/or other information to computer system 800 via storage device 824 (e.g., a removable disk drive, a flash drive, etc.) and/or network interface device 840. A network interface device, such as network interface device 840, may be utilized for connecting computer system 800 to one or more of a variety of networks, such as network 844, and one or more remote devices 848 connected thereto. Examples of a network interface device include, but are not limited to, a network interface card (e.g., a mobile network interface card, a LAN card), a modem, and any combination thereof. Examples of a network include, but are not limited to, a wide area network (e.g., the Internet, an enterprise network), a local area network (e.g., a network associated with an office, a building, a campus or other relatively small geographic space), a telephone network, a data network associated with a telephone/voice provider (e.g., a mobile communications provider data and/or voice network), a direct connection between two computing devices, and any combinations thereof. A network, such as network 844, may employ a wired and/or a wireless mode of communication. In general, any network topology may be used. Information (e.g., data, software 820, etc.) may be communicated to and/or from computer system 800 via network interface device 840.

Computer system 800 may further include a video display adapter 852 for communicating a displayable image to a display device, such as display device 836. Examples of a display device include, but are not limited to, a liquid crystal display (LCD), a cathode ray tube (CRT), a plasma display, a light emitting diode (LED) display, and any combinations thereof. Display adapter 852 and display device 836 may be utilized in combination with processor 804 to provide graphical representations of aspects of the present disclosure. In addition to a display device, computer system 800 may include one or more other peripheral output devices including, but not limited to, an audio speaker, a printer, and any combinations thereof. Such peripheral output devices may be connected to bus 812 via a peripheral interface 856. Examples of a peripheral interface include, but are not limited to, a serial port, a USB connection, a FIREWIRE connection, a parallel connection, and any combinations thereof.

The foregoing has been a detailed description of illustrative embodiments of the invention. Various modifications and additions can be made without departing from the spirit and scope of this invention. Features of each of the various embodiments described above may be combined with features of other described embodiments as appropriate in order to provide a multiplicity of feature combinations in associated new embodiments. Furthermore, while the foregoing describes a number of separate embodiments, what has been described herein is merely illustrative of the application of the principles of the present invention. Additionally, although particular methods herein may be illustrated and/or described as being performed in a specific order, the ordering is highly variable within ordinary skill to achieve methods, systems, and software according to the present disclosure. Accordingly, this description is meant to be taken only by way of example, and not to otherwise limit the scope of this invention.

Exemplary embodiments have been disclosed above and illustrated in the accompanying drawings. It will be understood by those skilled in the art that various changes, omissions and additions may be made to that which is specifically disclosed herein without departing from the spirit and scope of the present invention.

What is claimed is:

1. A system for retrieving patient information using large language models, the system comprising:
   at least a processor; and
   a memory communicatively connected to the at least a processor, the memory containing instructions configuring the at least a processor to:
   receive a natural language query as a function of a user input;
   input the natural language query into a large language model communicatively connected to the least a processor;
   receive a computer language query comprising a plurality of nodes from the large language model;
   map the plurality of nodes to one or more entries in a patient database;
   receive a database response from the patient database as a function of the mapping;
   generate a final database query as a function of the database response;
   query the patient database using the final database query;
   receive a user response as a function of the final database query; and
   transmit the user response to a graphical user interface as a function of the final database query, wherein transmitting the user response to the graphical user interface comprises:
   transmitting the user response to the large language model;
   generating a natural language response using the large language model, wherein generating the natural language response comprises:
   receiving a user profile comprising previously received natural language queries associated with the user;
   iteratively training a classifier as a function training data comprising exemplary natural language query inputs correlated to at least one exemplary language grouping output;
   classifying the user profile to one or more language groupings as a function of the trained classifier and the previously received natural language queries; and generating the natural language response as a function of as a function of the user response and the one or more language groupings; and transmitting the natural language response to the graphical user interface.

2. The system of claim 1, wherein transmitting the user response to the graphical user interface as a function of the final database query comprises:

generating a user interface data structure comprising at least the user response; and transmitting the user response to the graphical user interface as a function of the user interface data structure.

3. The system of claim 1, wherein receiving the natural language query as a function of the user input comprises receiving the natural language query using a chatbot system.

4. The system of claim 1, wherein receiving the computer language query comprising the plurality of nodes from the large language model comprises:

identifying one or more atomic elements as a function of the natural language query; and generating the computer language query as a function of the one or more atomic elements.

5. The system of claim 4, wherein receiving the database response from the patient database comprises extracting one or more patient cohorts as a function of the one or more atomic elements.

6. The system of claim 4, wherein generating the final database query as a function of the database response comprises:

generating a plurality of logical relationships between the plurality of nodes as a function of the database response; and generating the final database query as a function of the plurality of logical relationships and the database response.

7. The system of claim 6, wherein generating the plurality of logical relationships comprises determining a temporal relationship between the one or more atomic elements within the natural language query.

8. A method for retrieving patient information using large language models, the method comprising:

receiving, by at least a processor, a natural language query as a function of a user input;

inputting, by the at least a processor, the natural language query into a large language model communicatively connected to the least a processor;

receiving, by the at least a processor, a computer language query comprising a plurality of nodes from the large language model;

mapping, by the at least a processor, the plurality of nodes to one or more entries in a patient database;

receiving, by the at least a processor, a database response from the patient database as a function of the mapping;

generating, by the at least a processor, a final database query as a function of the database response;

querying, by the at least a processor, the patient database using the final database query;

receiving by the at least a processor, a user response as a function of the final database query; and transmitting, by the at least a processor, the user response to a graphical user interface as a function of the final database query, wherein transmitting the user response to the graphical user interface comprises:

transmitting the user response to the large language model;

generating a natural language response using the large language model, wherein generating the natural language response comprises:

receiving a user profile comprising previously received natural language queries associated with the user;

iteratively training a classifier as a function training data comprising exemplary natural language query inputs correlated to at least one exemplary language grouping output;

classifying the user profile to one or more language groupings as a function of the trained classifier and the previously received natural language queries; and generating the natural language response as a function of as a function of the user response and the one or more language groupings; and transmitting the natural language response to the graphical user interface.

9. The method of claim 8, wherein transmitting, by the at least a processor, the user response to the graphical user interface as a function of the final database query comprises:

generating a user interface data structure comprising at least the user response; and transmitting the user response to the graphical user interface as a function of the user interface data structure.

10. The method of claim 8, wherein receiving, by the at least a processor, the natural language query as a function of the user input comprises receiving the natural language query using a chatbot system.

11. The method of claim 8, wherein receiving, by the at least a processor, the computer language query comprising the plurality of nodes from the large language model comprises:

identifying one or more atomic elements as a function of the natural language query; and generating the computer language query as a function of the one or more atomic elements.

12. The method of claim 11, wherein receiving, by the at least a processor, the database response from the patient database comprises extracting one or more patient cohorts as a function of the one or more atomic elements.

13. The method of claim 11, wherein generating, by the at least a processor, the final database query as a function of the database response comprises:

generating a plurality of logical relationships between the plurality of nodes as a function of the database response; and generating the final database query as a function of the plurality of logical relationships and the database response.

14. The method of claim 13, wherein generating the plurality of logical relationships comprises determining a temporal relationship between the one or more atomic elements within the natural language query.

* * * * *